United States Patent
Miller et al.

(10) Patent No.: US 10,130,344 B2
(45) Date of Patent: Nov. 20, 2018

(54) MAGNETIC FIELD-COMPATIBLE COMPONENTS OF A MEDICAL DIAGNOSTIC AND/OR THERAPEUTIC SYSTEM

(71) Applicant: St. Jude Medical, Atrial Fibrillation Division, Inc., St. Paul, MN (US)

(72) Inventors: Stephan P. Miller, Vadnais Heights, MN (US); Ryan M. Albu, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 15/205,771

(22) Filed: Jul. 8, 2016

(65) Prior Publication Data

US 2017/0014112 A1   Jan. 19, 2017

Related U.S. Application Data

(63) Continuation of application No. 13/563,239, filed on Jul. 31, 2012, now Pat. No. 9,386,967.

(51) Int. Cl.
 *A61B 17/00* (2006.01)
 *G01R 33/025* (2006.01)
 (Continued)

(52) U.S. Cl.
 CPC .............. *A61B 17/00* (2013.01); *A61B 34/20* (2016.02); *G01R 33/025* (2013.01);
 (Continued)

(58) Field of Classification Search
 CPC ......... A61B 17/00; A61B 34/20; A61B 34/30; A61B 2034/2051; A61B 2034/301;
 (Continued)

(56) References Cited

U.S. PATENT DOCUMENTS 5,181,859 A   1/1993   Foreman et al.
5,324,311 A   6/1994   Acken
(Continued)

FOREIGN PATENT DOCUMENTS

GB   2269941 A   2/1994
WO   2008115945 A1   9/2008

OTHER PUBLICATIONS

Kam, Dong Gun et al., "A New Twisted Differential Line Structure on High-Speed Printed Circuit Boards to Enhance Immunity to Crosstalk and External Noise;" IEEE Microwave and Wireless Components Letters, vol. 13, No. 9, Reference pp. 411-413; Publication Date: Sep. 2003.

*Primary Examiner* — Sanjay Cattungal
(74) *Attorney, Agent, or Firm* — Dykema Gossett PLLC

(57) ABSTRACT

A medical device assembly comprises a medical device comprising a shaft having proximal and distal end portions. The device further comprises a sensor at the distal end portion of the shaft that comprises first and second leads extending therefrom to the proximal end portion of the shaft. The device further comprises an electromechanical connector having a plurality of pins at a first end thereof. First and second of the pins are electrically connected to the first and second sensor leads, respectively, thereby forming a first partial magnetic loop between the first and second pins. The connector further comprises first and second jumpers electrically connecting the first pin and third pins, and second and fourth pins, respectively, thereby forming a second partial magnetic loop. The partial magnetic loops are configured to combine with partial magnetic loops of another connector to form a pair of magnetic noise cancellation loops.

20 Claims, 21 Drawing Sheets

(51) Int. Cl.
*H01R 13/648* (2006.01)
*A61B 34/30* (2016.01)
*A61B 34/20* (2016.01)

(52) U.S. Cl.
CPC .......... H01R 13/648 (2013.01); *A61B 34/30* (2016.02); *A61B 2017/0046* (2013.01); *A61B 2017/00477* (2013.01); *A61B 2034/2051* (2016.02); *A61B 2034/301* (2016.02)

(58) Field of Classification Search
CPC .. A61B 2017/00477; A61B 2017/0046; H01R 13/648; G01R 33/025
See application file for complete search history.

(56) References Cited

U.S. PATENT DOCUMENTS

| | | | |
|---|---|---|---|
| 5,501,615 A | 3/1996 | Inaba et al. | |
| 6,233,476 B1 | 5/2001 | Strommer et al. | |
| 6,302,739 B1 | 10/2001 | Deno et al. | |
| 6,498,944 B1 | 12/2002 | Ben-Haim et al. | |
| 6,564,084 B2 | 5/2003 | Allred, III et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,386,339 B2 | 6/2008 | Strommer et al. | |
| 7,850,492 B1 | 12/2010 | Straka et al. | |
| 2002/0013102 A1 | 1/2002 | Kayworth et al. | |
| 2002/0151224 A1 | 10/2002 | Liao | |
| 2006/0046537 A1 | 3/2006 | Chong et al. | |
| 2008/0306380 A1 | 12/2008 | Parchak et al. | |
| 2011/0177474 A1* | 7/2011 | Jamnia ........... A61B 17/320068 | 433/119 |
| 2013/0026978 A1* | 1/2013 | Cooley .............. H01M 10/052 | 320/107 |
| 2013/0074614 A1* | 3/2013 | Holmes ............... B01L 3/50825 | 73/864.01 |
| 2013/0078625 A1* | 3/2013 | Holmes .............. G01N 35/0092 | 435/6.11 |
| 2013/0079236 A1* | 3/2013 | Holmes .................. G01N 33/50 | 506/9 |
| 2013/0079599 A1* | 3/2013 | Holmes ................. G06F 19/366 | 600/300 |

* cited by examiner

MAGNETIC FIELD-COMPATIBLE COMPONENTS OF A MEDICAL DIAGNOSTIC AND/OR THERAPEUTIC SYSTEM

CROSS-REFERENCE TO RELATED APPLICATIONS

This application is a continuation of U.S. application Ser. No. 13/563,239, filed 31 Jul. 2012 (hereinafter the '239 application), now U.S. Ser. No. 9,386,967, issued Jul. 12, 2016. The '239 application is hereby incorporated by reference as though fully set forth herein.

BACKGROUND OF THE INVENTION a. Field of the Invention

This disclosure relates to a system for performing one or more diagnostic and/or therapeutic medical procedures, the system comprising, in part, a magnetic field-based medical positioning system. More particularly, this disclosure relates to various components of the system for performing one or more diagnostic and/or therapeutic medical procedures, wherein the components are configured for use in a magnetic field environment created by the magnetic field-based medical positioning system.

b. Background Art

A number of different types of medical positioning systems may be used to aid in the performance of various medical diagnostic and therapeutic procedures relating to different parts of the human anatomy, such as, for example, the heart. Among other things, and generally speaking, these systems may provide the ability to determine the position and orientation (P&O) of one or more medical devices disposed within the body of the patient, such as, for example, catheters and sheaths, for visualization and navigation purposes.

One such type of medical positioning system is a magnetic field-based medical positioning system. Magnetic field-based systems generally include one or more magnetic field generators attached to or placed near the patient bed or another component in the operating environment. The field generators are configured to provide controlled, low-strength AC magnetic fields in an area of interest (i.e., an anatomical region) that are used to determine and track the P&O of one or more magnetic sensors disposed in or on a medical device disposed within the area of interest. More particularly, each magnetic sensor, which may comprise a magnetic coil, is configured to detect and generate a respective signal indicative of one or more characteristics of the magnetic field(s). The medical positioning system then processes the generated signals to produce one or more P&O readings associated with the sensors (and thus the medical device). The P&O of the medical device can thereafter be tracked relative to the magnetic field(s).

As briefly described above, medical devices that may be used with such medical positioning systems include elongate medical devices such as catheters and sheaths. These medical devices generally comprise an elongate shaft having a proximal end portion, a distal end portion, and one or more sensors mounted in or on the shaft at or near the distal end portion thereof. As also briefly described above, the sensors of the medical device may comprise magnetic sensors in the form of coils that are configured to allow the system to determine the P&O of the sensor, and therefore by extension, the medical device. More particularly, each sensor may comprise a loop of wire wound a predetermined number of times around a small diameter core to form a coil having a size that is suitable for packaging within the shaft of the medical device, and for generating a current when placed in a magnetic field that is used by the system to determine the P&O of the sensor.

One drawback to the use of these types of medical devices in conjunction with a magnetic field-based medical positioning system is that any loops of wire that are considered separate or apart from the sensor can act as a magnetic pickup when subjected to magnetic fields. This may result in noise or interference being added to the signal generated by the sensor, thereby potentially adversely impacting the accuracy of the P&O determination based thereon (i.e., causing an error in the P&O of the sensor determined based on the signal generated by the sensor). For example, a wire that is wrapped numerous times around a core to form a coil may have two ends or leads extending from the coil. These leads are routed from the coil down the shaft of the medical device where they are terminated in an electrical connector that allows for the sensor to be electrically coupled to other components of, for example, the medical positioning system or components that are intermediate thereto (e.g., amplifiers, processors, etc.). However, when arranged within the shaft of the medical device, these two leads may serve to form a loop of wire that may generate a current when subjected or exposed to a magnetic field. As described above, this may result in the addition of noise or interference to the current signal being transmitted from the sensor.

One conventional technique used to address the above-described problem is to arrange the two leads in a twisted pair pattern along the lengths of the leads from the sensor to the termination point. Such an arrangement is known to prevent, or at least substantially minimize, magnetic pickup in the wires. Accordingly, by preventing magnetic pickup along the length of the shaft of the medical device, interference or noise that may adversely impact the signals generated and transmitted by the sensor is prevented or at least substantially minimized. However, while this technique has been useful in limiting interference generated along the length of the shaft of the medical device, it does not completely solve the problem with respect to other areas or locations of the medical device or within the system of which it is a part.

More particularly, as described above, the two leads of the sensor are terminated at an electrical connector that may be disposed at or near the proximal end portion of the shaft (e.g., within or near the handle of the device located proximate the proximal end portion of the shaft). To do so, the two leads are typically untwisted in order to be coupled (e.g., soldered, crimped, etc.) to respective pins of the electrical connector. However, the length of the pins, the relatively large distance therebetween, and the length of the untwisted portion of the leads proximate the connector combine to form a loop comprised of the pins of the connector and the untwisted portions of the leads. Because the handle portion of the medical device, and therefore, the electrical connector to which the leads are coupled, is disposed in close proximity to the patient during a procedure, the electrical connector may be subjected or exposed to the magnetic field(s) applied by the medical positioning system. As a result, the loop formed by the untwisted portion of the leads and the pins of the electrical connector can act as a magnetic pickup, and therefore, a current may be induced in the loop by the magnetic field(s). As described above, such a generated current may result in noise or interference to the signal generated and transmitted by the sensor, which may introduce not in significant error in the sensor location determined therefrom.

The foregoing discussion is intended only to illustrate the present field and should not be taken as a disavowal of claim scope.

BRIEF SUMMARY OF THE INVENTION

In various embodiments, the present invention is generally directed to a medical device assembly configured for use in a magnetic field environment.

In accordance with one aspect of the invention and the present teachings, a medical device assembly for use in a magnetic field environment is provided. In an exemplary embodiment, the medical device assembly comprises a medical device. The medical device, in turn, comprises an elongate shaft having a proximal end portion and a distal end portion. The medical device further comprises a positioning sensor disposed at the distal end portion of the shaft and comprising first and second leads arranged in a twisted pair pattern and extending from a sensing element of the sensor to the proximal end of the shaft. The medical device still further comprises an electromechanical connector having a first end, a second end, and a plurality of pins disposed at the first end thereof, wherein first and second pins of the plurality of pins are electrically connected to the first and second leads of the sensor, respectively, thereby forming a first partial magnetic loop between the first and second pins.

In an exemplary embodiment, the connector of the medical device further comprises a first electrical jumper electrically connecting the first pin with a third pin of the plurality of pins, and a second electrical jumper electrically connecting the second pin with a fourth pin of the plurality of pins, thereby forming a second partial magnetic loop between the third and fourth pins. In an exemplary embodiment, the first and second partial magnetic loops are substantially parallel to each other. The first and second partial magnetic loops are configured to combine with respective first and second partial magnetic loops of a complementary electromechanical connector configured to be mated with the second end of the electromechanical connector of the medical device to form first and second magnetic noise cancellation loops that are substantially equal in area and opposite in orientation.

In accordance with another aspect of the invention and the present teachings, an electrical cable configured for use in a magnetic field environment is provided. In an exemplary embodiment, the cable comprises a sheath having a first end and a second end. The cable further comprises first and second electrical conductors disposed within the sheath and arranged in a twisted pair pattern, wherein the first and second electrical conductors extend between the first and second ends of the sheath. The cable still further comprises first and second electromechanical connectors disposed at the first and second ends of said sheath, respectively, wherein each of the first and second connectors comprises a first end, a second end, and a plurality of pins disposed at the first end thereof. The first and second electrical conductors of the cable are electrically connected to first and second pins of the plurality of pins, respectively, thereby forming a first partial magnetic loop between the first and second pins. Each of the first and second connectors further comprises a first electrical jumper electrically connecting the first pin with a third pin of the plurality of pins, and a second electrical jumper electrically connecting the second pin with a fourth pin of the plurality of pins, thereby forming a second partial magnetic loop between the third and fourth pins. In an exemplary embodiment, the first and second partial loops are substantially parallel to each other.

In accordance with another aspect of the invention and the present teachings, a junction box configured for use with a medical device in a magnetic field environment is provided. In an exemplary embodiment, the junction box comprises a housing having a top side, a bottom side, and a plurality of side walls extending between the top and bottom sides. The junction box further comprises an electromechanical connector disposed in one of the plurality of side walls, wherein the electromechanical connector comprises a first end, a second end, and a plurality of pins disposed at the first end thereof. In an exemplary embodiment, first and second pins of the plurality of pins are electrically connected to first ends of respective first and second electrical conductors disposed within the housing thereby forming a first partial magnetic loop between the first and second pins. The connector further comprises a first electrical jumper electrically connecting the first pin with a third pin of the plurality of pins, and a second electrical jumper electrically connecting the second pin with a fourth pin of the plurality of pins, thereby forming a second partial magnetic loop that, in an exemplary embodiment, is parallel to the first partial magnetic loop. The first and second partial magnetic loops are configured to combine with respective first and second partial magnetic loops of a complementary electromechanical connector when the second end of the electromechanical connector of the junction box is mated with the complementary connector to form first and second magnetic noise cancellation loops that are substantially equal in area and opposite in orientation.

In accordance with another aspect of the invention and the present teachings, an electromechanical connection assembly for use in a magnetic field environment is provided. In an exemplary embodiment, the electromechanical connector assembly comprises first and second electromechanical connectors each having a first end and second end, wherein the second ends of the connectors are configured to be mated with each other. Each of the first and second electromechanical connectors further comprise a plurality of pins disposed at the first end thereof, wherein first and second pins of the plurality of pins are electrically connected to first and second electrical conductors, respectively, thereby forming first partial magnetic loops between the first and second pins. Each of the connectors further comprises a first electrical jumper electrically connecting the first pin thereof with a third pin of the plurality of pins, and a second electrical jumper electrically connecting the second pin thereof with a fourth pin of the plurality of pins, thereby forming second partial magnetic loops between the third and fourth pins. In such an embodiment, the first and second partial magnetic loops of the first connector are configured to combine with the respective first and second partial magnetic loops of the second connector when the second ends of the first and second connectors are mated with each other to form first and second magnetic noise cancellation loops that are substantially equal in area and opposite in orientation.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Various embodiments are described herein of various apparatus and/or systems. Numerous specific details are set forth to provide a thorough understanding of the overall structure, function, manufacture, and/or use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
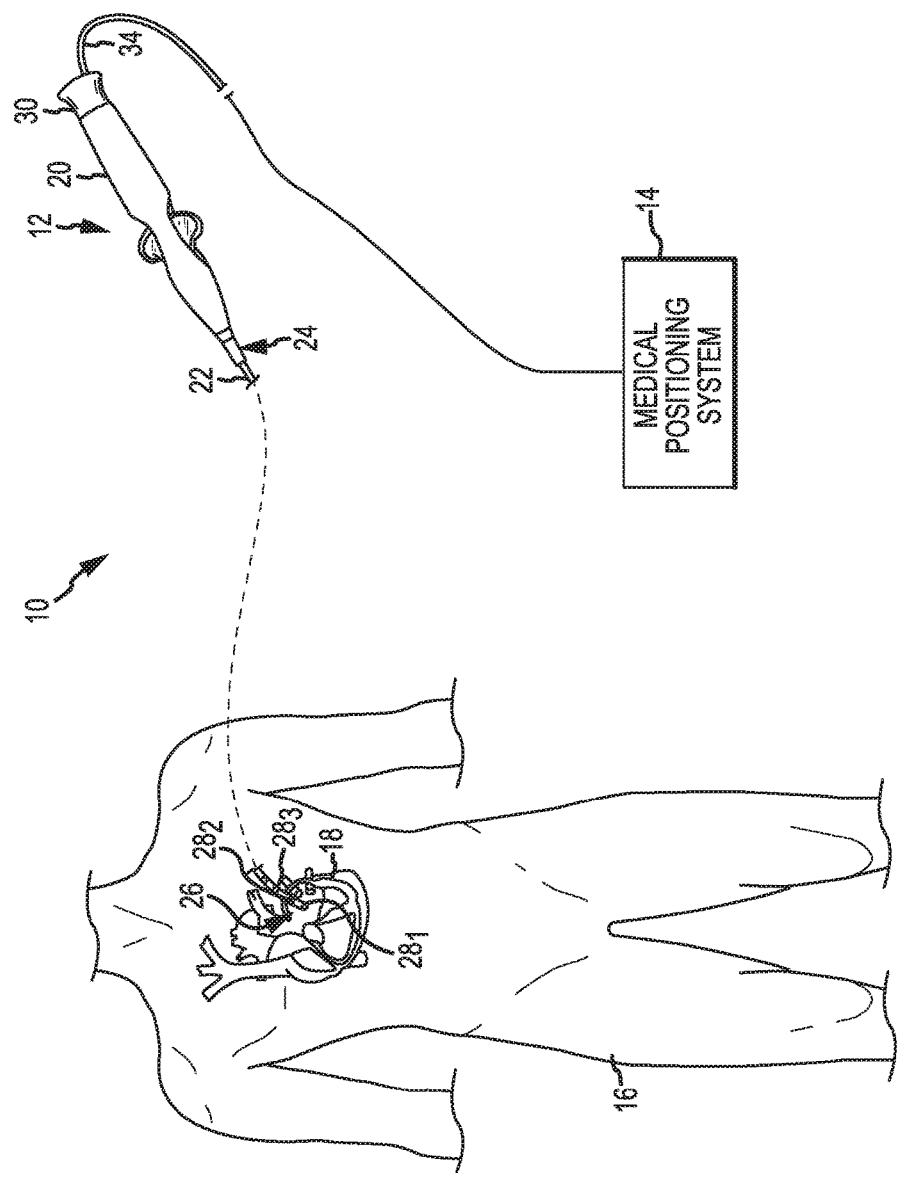
FIG. 1 is a diagrammatic view of an exemplary system for performing one or more diagnostic or therapeutic procedures, wherein the system comprises a magnetic field-based medical positioning system, in accordance with the present teachings.

Referring now to the drawings wherein like reference numerals are used to identify identical or similar components in the various views, FIG. 1 illustrates one exemplary embodiment of a system 10 for performing one or more diagnostic and/or therapeutic medical procedures relating to different parts of the human anatomy, such as, for example, the heart. For purposes of clarity and illustration, the description set forth below will be with respect to a system used for cardiac-related applications only. It should be understood, however, that the present disclosure may be implemented and find use in connection with any number of other anatomical-related applications. Accordingly, the present disclosure is not intended to be limited to cardiac-related applications.

In an exemplary embodiment, and with reference to FIG. 1, the system 10 comprises a medical device 12 and a medical positioning system 14. The medical device 12 may comprise an elongate medical device such as, for example, catheter or a sheath. For purposes of illustration and clarity, the description below will be limited to an embodiment wherein the medical device 12 comprises a catheter (catheter 12). It will be appreciated, however, that the present disclosure is not meant to be limited to such an embodiment, but rather in other exemplary embodiments, the medical device may comprise other elongate medical devices, such as, for example and without limitation, sheaths, introducers and the like.

With continued reference to FIG. 1, the catheter 12 is configured to be inserted into a patient's body 16, and more particularly, into the patient's heart 18. The catheter 12 may include a handle 20, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, ... $28_N$, as appropriate and as generally illustrated. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads. In an exemplary embodiment, the catheter 12 further comprises an electromechanical connector 30 configured to allow the catheter 12, and the sensors 28 thereof, in particular, to be coupled with other components of the system 10, such as, for example, the medical positioning system 14.

The handle 20, which is disposed at the proximal end portion 24 of the shaft 22, provides a location for the clinician to hold the catheter 12 and may further provide means for steering or guiding the shaft 22 within the body 16 of a patient. For example, the handle 20 may include means to manipulate one or more steering wires extending through the catheter 12 to the distal end portion 26 of the shaft 22 to steer the shaft 22. The handle 20 is conventional in the art and it will be understood that the construction of the handle 20 may vary. In another exemplary embodiment, the catheter 12 may be robotically driven or controlled. Accordingly, in such an embodiment, rather than a clinician manipulating a handle to steer or guide the catheter 12, and the shaft 22 thereof, in particular, a robot is used to manipulate the catheter 12.

The shaft 22 is an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and defines one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an exemplary embodiment, one or more of the sensors 28 are provided to perform a location or position sensing function. More particularly, and as will be described in greater detail below, one or more of the sensors 28 are configured to be a positioning sensor that provides information relating to the location (position and orientation, or "P&O") of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment wherein a single sensor 28 of the catheter 12 comprises a positioning sensor. It will be appreciated, however, that in other exemplary embodiments, which remain within the spirit and scope of the present disclosure, the catheter 12 may comprise more than one positioning sensor as well as other sensors or electrodes configured to perform other diagnostic and/or therapeutic functions. As will be described in greater detail below, the sensor 28 comprises a pair of leads $32_1$, $32_2$ extending from a sensing element thereof (e.g., a coil) that are configured to electrically couple the sensor 28 to other components of the system 10, such as, for example, the medical positioning system 14.

Figure 2:
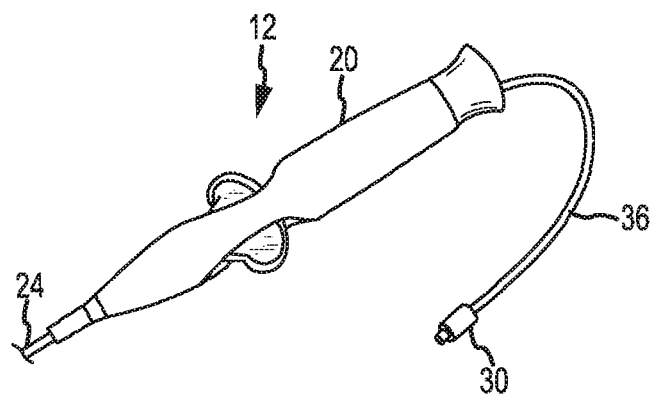
FIG. 2 is a diagrammatic view of a portion of an elongate medical device, such as, for example, a catheter, configured for use in the system illustrated in FIG. 1.

As will be described in greater detail below, the electromechanical connector 30 provides electrical and mechanical connection(s) for, among other things, the leads $32_1$, $32_2$ of the sensor 28 of the catheter 12, as well as wires or cables, such as, for example, a cable 34 extending between the catheter 12 and other components of the system 10 (e.g., the medical positioning system 14, an ablation generator, an electrophysiology recording system, a junction box, a stimulation system, a tissue contact sensing system, etc.). In an exemplary embodiment, and as illustrated in FIG. 1, the connector 30 is disposed within the handle 20 of the catheter 12. In another exemplary embodiment, rather than being disposed within or as part of the handle 20, the connector 30 is disposed apart from the handle 20. For example, and as illustrated in FIG. 2, the connector 30 may be disposed at the end of a pigtail 36 extending from the handle 20 of the medical device 12.

Figure 3:
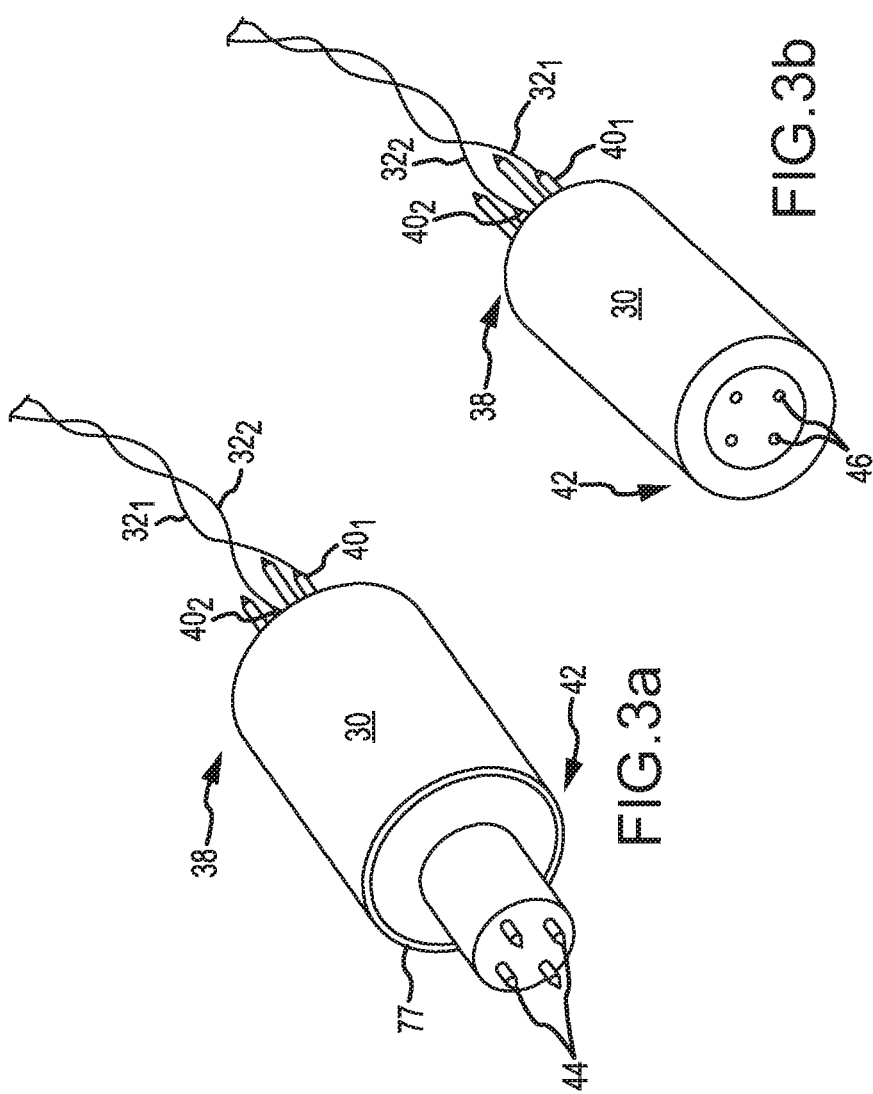
FIGS. 3a and 3b are isometric views of alternate exemplary embodiments of an electromechanical connector of the medical device illustrated in FIG. 2.

Regardless of where the connector 30 is located, in an exemplary embodiment such as that illustrated in FIGS. 3a and 3b, a first end 38 of the connector 30 has a plurality of pins 40, and each lead of the pair of leads $32_1$, $32_2$ of the sensor 28 is electrically and mechanically connected or coupled to a respective one of the pins 40. As used herein, "pin 40" or "pins 40" may refer to one or more pins $40_1$, $40_2$, ... $40_N$, as appropriate and as generally illustrated. A second end 42 of the connector 30 opposite the first end 38 is configured to provide an interface between the catheter 12, and the sensor 28 thereof, in particular, and other components of the system 10, such as, for example, the medical positioning system 14 or a junction box. For example, in an exemplary embodiment such as that illustrated in FIG. 3a, the second end 42 of the connector 30 may take the form of a male plug connector having a plurality of pins 44 that are electrically coupled to, or that comprise, the pins 40 disposed at the first end 38 of the connector 30 (e.g., the pins 40 may extend through the first and second ends 38, 42 of the connector 30). In such an embodiment, the second end 42 of the connector 30 is configured to be mated with a complementary female receptacle connector having a plurality of socket contacts configured to receive the pins 44 of the connector 30. Alternatively, as illustrated in FIG. 3b, the second end 42 of the connector 30 may take the form of a female receptacle connector having a plurality of sockets 46 configured to receive a corresponding number of pins from a complementary male plug connector of a cable.

Accordingly, regardless of the particular form the connector 30 takes, it is configured to allow for the electrical connection of the catheter 12, and the sensor 28 thereof, to one or more components of the system 10, such as, for example, the medical positioning system 14.

Figure 4:
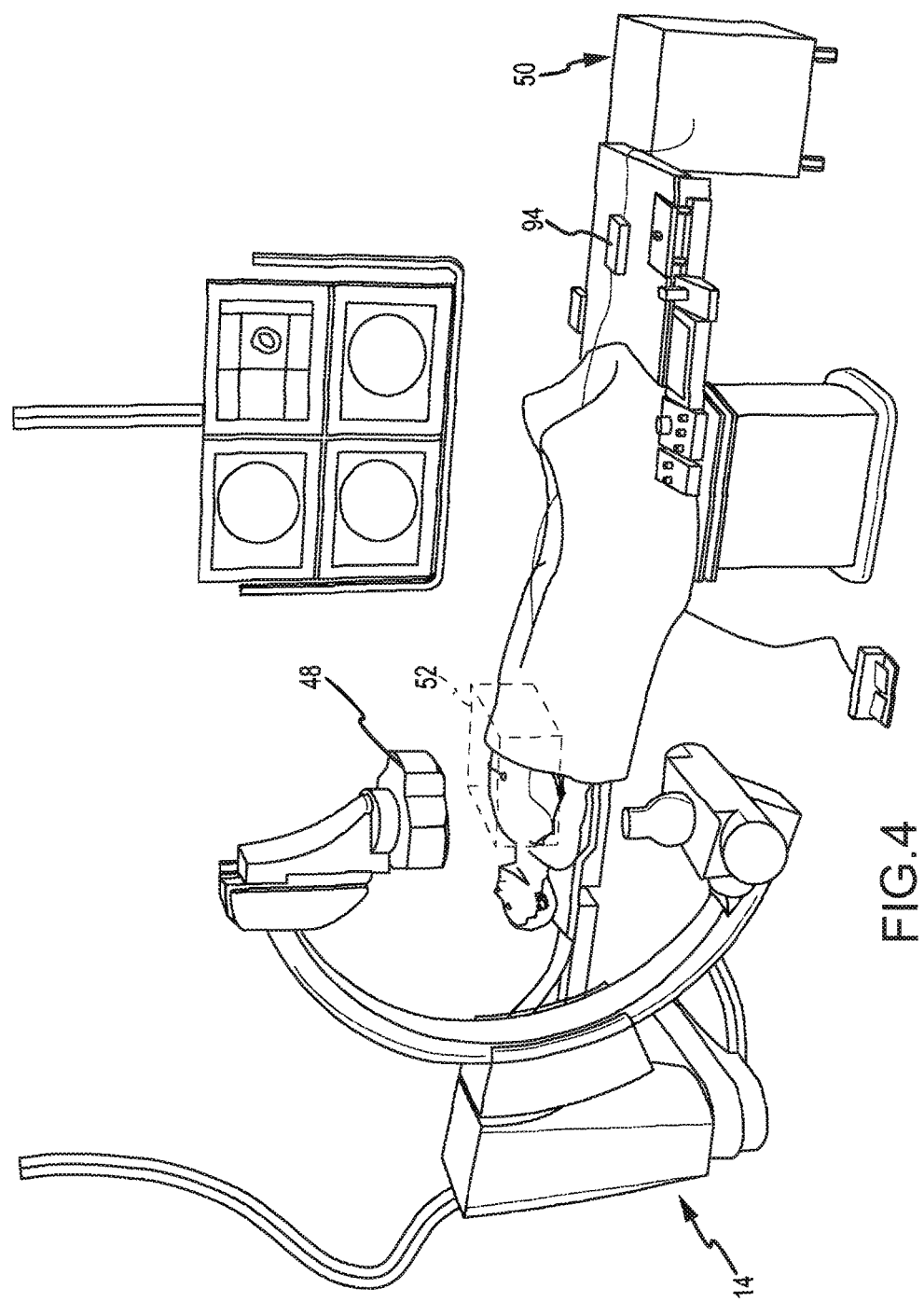
FIG. 4 is a diagrammatic view of an exemplary magnetic field-based medical positioning system configured for use in the system illustrated in FIG. 1.

With reference to FIGS. 1 and 4, the medical positioning system 14 will now be described. The medical positioning system 14 is provided for determining the P&O of the sensor 28 of the catheter 12, and thus, the P&O of the catheter 12. In an exemplary embodiment, the medical positioning system 14 may comprise a magnetic field-based system such as, for example, the Carto™ System available from Biosense Webster, and as generally shown with reference to one or more of U.S. Pat. Nos. 6,498,944; 6,788,967; and 6,690,963, the entire disclosures of which are incorporated herein by reference, or the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference. Alternatively, the medical positioning system 14 may comprise a combination magnetic field-based system and electric field-based system such as, for example and without limitation, the Carto 3™ System also available from Biosense Webster.

In exemplary embodiment, and in general terms, the medical positioning system 14 comprises, at least in part, a magnetic transmitter assembly (MTA) 48 and a magnetic processing core 50 for making P&O determinations. The MTA 48 is configured to generate low-strength magnetic field(s) in and around the patient's chest cavity in a predefined three-dimensional space designated as motion box 52 in FIG. 4. In such an embodiment, and as briefly described above, the catheter 12 includes a positioning sensor 28 comprising a magnetic sensor configured to detect one or more characteristics of the low-strength magnetic field(s) applied by the MTA 48 when the sensor 28 is disposed within the motion box 52. The sensor 28, which in an exemplary embodiment comprises a magnetic coil, is electrically connected to the processing core 50 and configured to generate a signal corresponding to the sensed characteristics of the magnetic field(s) that is provided to the magnetic processing core 50. The processing core 50 is responsive to the detected signal and is configured to calculate a three-dimensional P&O reading for the sensor 28. Thus, the medical positioning system 14 enables real-time tracking of each magnetic sensor 28 of the catheter 12 in three-dimensional space, and therefore, real-time tracking of the catheter 12.

As described above, one drawback to the use of a magnetic field-based medical positioning system in conjunction with elongate medical devices, such as catheters, is that any loops of wire that are separate and distinct from the sensing element (e.g., coil) of the sensor 28 can act as a magnetic pickup when subjected to magnetic fields. As a result, noise or interference may be added to the signals generated by the sensor 28, thereby resulting in not insignificant errors being introduced into P&O determinations based on those signals. For example, and with reference to FIGS. 1-3b, in the instance wherein the sensor 28 comprises a magnetic coil formed by a wire wrapped numerous times around a core, the leads $32_1$, $32_2$ of the sensor 28 are routed from the coil down the shaft 22 of the catheter 12 to the proximal end thereof where they may be terminated in an electromechanical connector, such as, for example, the connector 30. More particularly, the leads $32_1$, $32_2$ may be coupled (e.g., soldered, crimped, etc.) to respective pins 40 of the connector 30. However, over the length of the shaft 22, the leads $32_1$, $32_2$ may form a loop of wire that may act as a magnetic pickup when subjected or exposed to a magnetic field, thereby causing interference to the signals generated by the sensor 28. To prevent this from occurring, the leads $32_1$, $32_2$ may be arranged in a twisted pair pattern along the lengths thereof from the sensing element of the sensor 28 to a point near the termination point of the leads $32_1$, $32_2$ at the connector 30.

Figure 5:
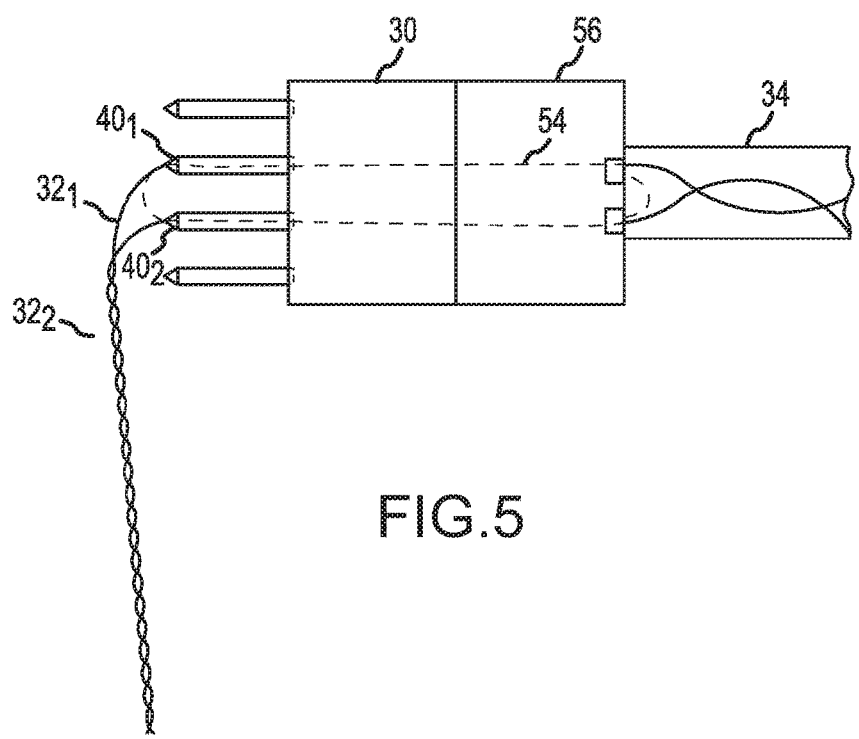
FIG. 5 is a diagrammatic view of a conventional connection arrangement between two electromechanical connectors illustrating a magnetic pickup loop created between the two connectors when the connectors are mated together.

While the twisted pair arrangement of the leads $32_1$, $32_2$ themselves is suitable to prevent the generation of noise within the leads $32_1$, $32_2$ along their length, it does not provide a complete solution to the problem. More particularly, in order to be connected to the pins 40 of the connector 30, the leads $32_1$, $32_2$ may be untwisted and then connected to respective pins 40. For example, in the embodiments illustrated in FIGS. 3a and 3b, the leads $32_1$, $32_2$ are untwisted and then coupled or connected to pins $40_1$, $40_2$, respectively. The combination of the untwisted portion of the leads $32_1$, $32_2$, the length of the pins 40 (e.g., $40_1$, $40_2$), and the relatively large distance or space between the pins 40 results in, as illustrated in FIG. 5, the formation of a magnetic loop 54 when the connector 30 is mated with a corresponding electromechanical connector 56 of a cable, such as, for example, the cable 34. Due to the location of the connection between the connector 30 and the connector 56, which is in relatively close proximity to the patient bed, this loop 54 may be subjected or exposed to the magnetic field(s) applied by the MTA 48, and therefore, may generate noise or interference in the signal generated by the sensor 28.

Figure 6:
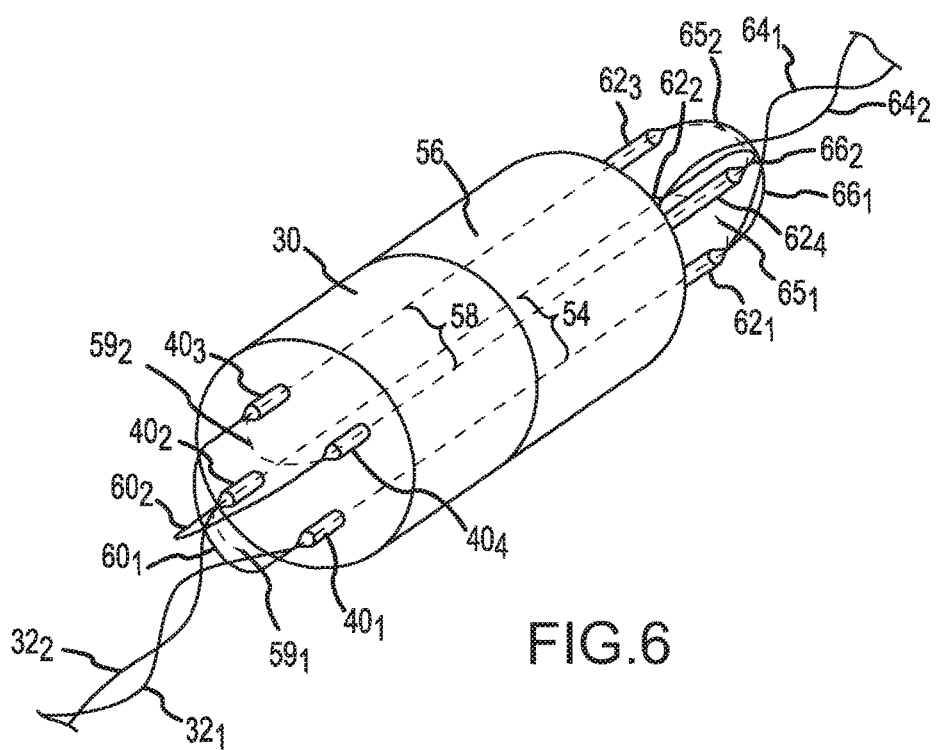
FIG. 6 is an isometric view of an exemplary embodiment of a connection arrangement between two electromechanical connectors comprising a pair of magnetic noise cancellation loops that are equal in area and opposite in orientation, in accordance with the present teachings.

One exemplary way to prevent, or at least minimize, the generation of noise or interference in the connection arrangement or assembly of the connector 30 and a complementary connector is illustrated in FIG. 6. In general terms, when the connector 30 is mated with a complementary connector (e.g., the connector 56), a second magnetic loop 58 is formed that is substantially equal in area and opposite in orientation to the magnetic loop 54. As such, when the connection between the connector 30 and connector 56 is subjected or exposed to a magnetic field, the currents induced in the two loops will be equal but opposite, thereby resulting in the currents offsetting each other. Thus, interference to the signals generated by the sensor 28 and transmitted through the connectors 30, 56 is prevented or at least substantially minimized.

More particularly, in order to form the two magnetic loops 54, 58, each connector 30, 56 includes a pair of partial magnetic loops that combine to form a pair of complete loops when the connectors 30, 56 are mated together. With respect to the connector 30, and as briefly described above, one partial loop (referred to as "partial loop $59_1$" below and represented by dotted or broken lines in FIG. 6) that corresponds to the magnetic loop 54 is formed by the pins $40_1$, $40_2$ and the untwisted portion of the leads $32_1$, $32_2$. As such, the partial loop $59_1$ is formed between the pins $40_1$, $40_2$. In an exemplary embodiment, the second partial magnetic loop (referred to as "partial loop $59_2$" below and also represented by dotted or broken lines in FIG. 6) that corresponds to the magnetic loop 58 may be formed by creating a pair of mechanical partial loops 60 between respective pairs of pins 40. As used herein, "loop 60" or "loops 60" may refer to one or more loops $60_1$, $60_2$, . . . $60_N$, as appropriate and as generally illustrated.

More particularly, each of the partial mechanical loops 60 comprises a pair of pins of the corresponding connector, with one pin of each pin pair being connected to a lead wire 32. For example, in the embodiment illustrated in FIG. 6, the sensor leads $32_1$, $32_2$ are electrically connected to pins $40_1$, $40_2$, respectively, of the connector 30. To form a first partial mechanical loop $60_1$, the pin $40_1$ is electrically connected or jumped to another pin 40 of the connector 30, namely, pin $40_3$, with a first electrical jumper. Similarly, to form a second partial mechanical loop $60_2$, the pin $40_2$ is electrically connected or jumped to another pin 40 of the connector 30, namely, pin $40_4$, with a second electrical jumper. When the two partial mechanical loops $60_1$, $60_2$ are in place, they act to form or create the partial magnetic loop $59_2$ between the pins $40_3$, $40_4$ that is substantially parallel to the partial magnetic loop $59_1$ between the pins $40_1$, $40_2$.

In order to create partial magnetic loops in the connector 30 that when combined with two other partial magnetic loops of a complementary connector to form two complete magnetic loops that are both equal in area and opposite in orientation, the two partial magnetic loops of each connector may also be equal in area and opposite in orientation relative to each other. To that end, in an exemplary embodiment, the pins 40 that are used to form the two partial magnetic loops $59_1$, $59_2$ of the connector 30 are arranged in a square with each pin 40 comprising a vertex of the square, and with the pins 40 that are connected to each other to form a partial mechanical loop 60 being diagonal from each other. For example, in the embodiment illustrated in FIG. 6, the pins $40_1$-$40_4$ are arranged in a square, with pin $40_1$ and pin $40_3$, which form partial mechanical loop $60_1$, being diagonal from each other, and pin $40_2$ and pin $40_4$, which form partial mechanical loop $60_2$, also being diagonal from each other. Further, in an exemplary embodiment, the partial mechanical loops $60_1$, $60_2$ may be substantially the same size or length as the length of the untwisted portion of the pair of leads $32_1$, $32_2$ that are connected to the pins 40 of the connector 30 (e.g., the partial mechanical loops $60_1$, $60_2$ may be substantially the same size as the untwisted portion of the leads $32_1$, $32_2$). In order to reduce or limit the area of the loops created in the manner described herein, in an exemplary embodiment, the pins $40_1$-$40_4$ are arranged to be as close to each other as possible.

Similarly, and with continued reference to FIG. 6, in an exemplary embodiment, the connector 56 of the cable 34 comprises a plurality of pins 62 (as used herein, "pin 62" or "pins 62" may refer to one or more pins $62_1$, $62_2$, . . . $62_N$, as appropriate and as generally illustrated) that comprise respective portions of a pair of partial magnetic loops of the connector 56. For example, in the embodiment illustrated in FIG. 6, the connector 56 comprises a pair of pins $62_1$, $62_2$ that are coupled to a pair of electrical conductors 64 (as used herein, "conductor 64" or "conductors 64" may refer to one or more conductors $64_1$, $64_2$, . . . $64_N$, as appropriate and as generally illustrated) of the cable 34. As with the connector 30 described above, the pins $62_1$, $62_2$ along with an untwisted portion of the electrical conductors $64_1$, $64_2$, serve to form a first partial magnetic loop $65_1$ that when combined with the partial magnetic loop $59_1$ of the connector 30 when the connectors 30, 56 are coupled together, form the complete magnetic loop 54.

As also with the connector 30 described above, a second partial magnetic loop $65_2$ may be formed by creating a pair of mechanical partial loops 66 between respective pairs of pins 62. When the connectors 30, 56 are coupled together, the second partial magnetic loop $65_2$ is combined with the partial magnetic loop $59_2$ of the connector 30 to form the complete magnetic loop 58.

More particularly, to form a first partial mechanical loop $66_1$, the pin $62_1$ is electrically connected or jumped to another pin 62 of the connector 56, namely, pin $62_3$, with a first electrical jumper. Similarly, to form a second partial mechanical loop $66_2$, the pin $62_2$ is electrically connected or jumped to another pin 62 of the connector 56, namely, pin $62_4$, with a second electrical jumper. When the two mechanical partial loops $66_1$, $66_2$ are in place, they act to form or create the partial magnetic loop $65_2$ between the pins $62_3$, $62_4$ that is substantially parallel to the partial magnetic loop $65_1$ between the pins $62_1$, $62_2$.

As with the partial magnetic loops 59 of the connector 30, in an exemplary embodiment, the pins 62 that are used to form the two partial magnetic loops $65_1$, $65_2$ of the connector 56 are arranged in a square with each pin 62 comprising a vertex of the square, and with the pins 62 that are connected to each other to form a partial mechanical loop $66_{1-N}$ being diagonal from each other. For example, in the embodiment illustrated in FIG. 6, the pins $62_1$-$62_4$ are arranged in a square, with pin $62_1$ and pin $62_3$, which form partial mechanical loop $66_1$, being diagonal from each other, and pin $62_2$ and pin $62_4$, which form partial mechanical loop $66_2$, also being diagonal from each other. Further, in an exemplary embodiment, the partial mechanical loops $66_1$, $66_2$ may be substantially the same size or length as the length of the untwisted portion of the pair of electrical conductors 64 that are connected to the pins 62 of the connector 56 (e.g., the mechanical loops $66_1$, $66_2$ may be substantially the same size as the untwisted portion of the electrical conductors $64_1$, $64_2$). In order to reduce or limit the area of the loops created in the manner described herein, in an exemplary embodiment, the pins $62_1$-$62_4$ are arranged to be as close to each other as possible.

In order for the partial magnetic loops 59 of the connector 30 and the partial magnetic loops 65 of the connector 56 to combine to form the complete magnetic loops, the pins 40 that form the partial magnetic loops 59 and the pins 62 that form the partial magnetic loops 65 may be connected to each other when the connectors 30, 56 are mated. More particularly, the pins of the respective connectors 30, 56 are arranged in manner that when the connectors are mated, the pin $40_1$ of the connector 30 is electrically connected to the pin $62_1$ of the connector 56, the pin $40_2$ is electrically connected to the pin $62_2$, the pin $40_3$ is electrically connected to the pin $62_3$, and the pin $40_4$ is electrically connected to the pin $62_4$.

Figure 7:
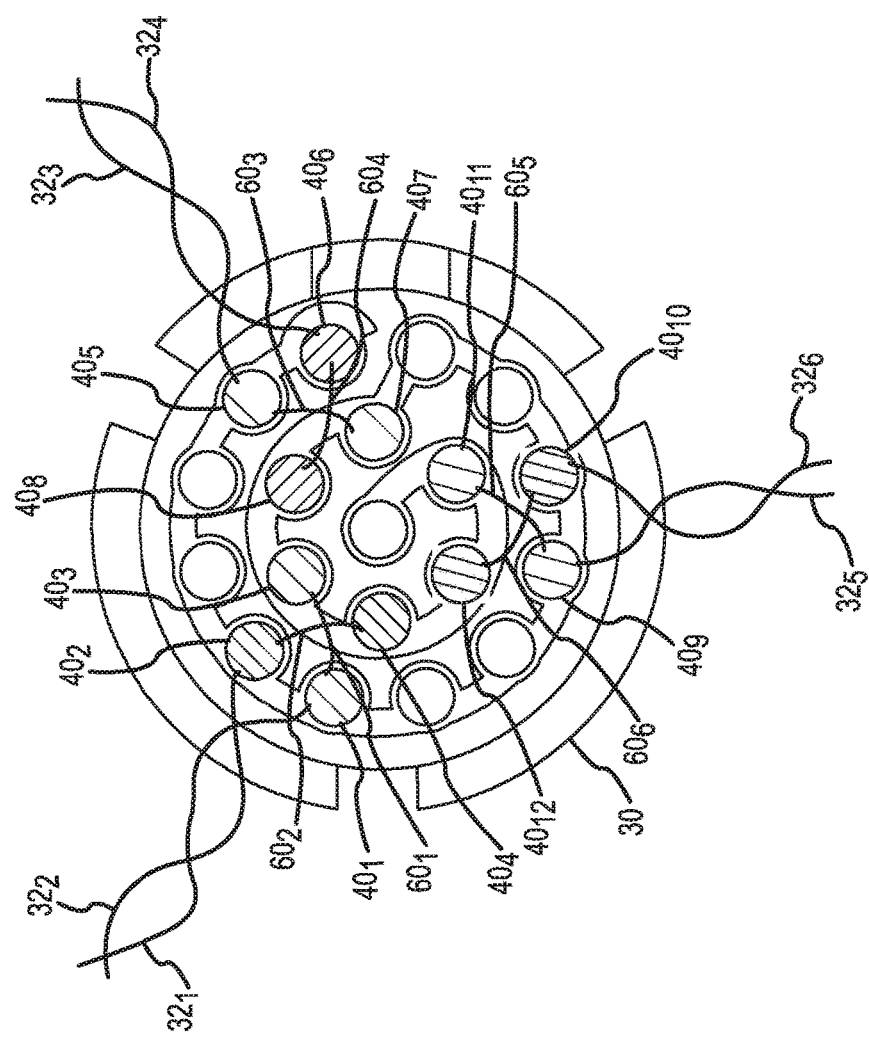
FIG. 7 is a plan and diagrammatic view of an end of an electromechanical connector, such as, for example, that depicted in FIG. 3a, configured to accommodate a plurality of sensor lead pairs and a plurality of corresponding pairs of partial loops between respective pairs of pins of the connector, in accordance with the present teachings.

It will be appreciated that while the description above has thus far been with respect to an embodiment wherein the catheter 12 comprises a single sensor 28, and therefore, comprises a single pair of leads $32_1$, $32_2$, such that the connectors 30, 56 each only include a pair of partial magnetic loops 59, 65, respectively, and therefore, a pair of partial mechanical loops 60, 66, respectively, the present disclosure is not meant to be so limited. Rather, in other exemplary embodiments, the catheter 12 may comprise a plurality of sensors 28, each having a pair of leads $32_1$, $32_{i+1}$ terminating at the connector 30. As such, the connectors 30, 56 may each comprise a pair of partial magnetic loops corresponding to each pair of leads $32_i$, $32_{i+1}$ (i.e., for each sensor 28). For instance, FIG. 7 illustrates an embodiment of the connector 30 configured to accommodate a catheter 12 having three sensors 28, each having a pair of leads $32_i$, $32_{i+1}$ (i.e., leads $32_1$, $32_2$; leads $32_3$, $32_4$; and leads $32_5$, $32_6$). Therefore, the connector 30 illustrated in FIG. 7 comprises three pairs of partial magnetic loops 59, and therefore, three pairs of partial mechanical loops 60 (i.e., loops $60_1$, $60_2$; loops $60_3$, $60_4$; and loops $60_5$, $60_6$).

More particularly, the leads $32_1$, $32_2$ are coupled to pins $40_1$, $40_2$. As described above, each of the pins $40_1$, $40_2$ are connected to a respective one of the other pins 40 of the connector 30—pins $40_3$, $40_4$, respectively—to form a pair of partial mechanical loops $60_1$, $60_2$. Similarly, the leads $32_3$, $32_4$ corresponding to another sensor 28 are coupled to pins $40_5$, $40_6$. As described above, each of the pins $40_5$, $40_6$ are connected to a respective one of the other pins 40 of the connector 30—pins $40_7$, $40_8$, respectively—to form a pair of partial mechanical loops $60_3$, $60_4$. Finally, the leads $32_5$, $32_6$ corresponding to yet another sensor 28 are coupled to pins $40_9$, $40_{10}$. As described above, each of the pins $40_9$, $40_{10}$ are connected to a respective one of the other pins 40 of the connector 30—pins $40_{11}$, $40_{12}$, respectively—to form a pair of partial mechanical loops $60_5$, $60_6$.

In such an embodiment, the connector 56 of the cable 34 would be similarly configured so as to form a pair of complete magnetic loops for each pair of leads 32, and therefore, for each sensor 28 when the connectors 30, 56 are mated. Accordingly, the connector 30, the cable 34, and the connector 56 thereof are each configured to accommodate the particular number of sensors 28 that the catheter 12 includes. However, for purposes of clarity and illustration, the description below will be limited to an embodiment wherein the catheter 12 comprises a single sensor 28, and therefore, a single pair of leads 32. Thus, the connectors 30, 56 will each comprise a pair of partial magnetic loops 59, 65, respectively, that combine to form a pair of complete magnetic loops 54, 58. However, it will be appreciated that, as described above, embodiments wherein the catheter 12 comprises a plurality of sensors 28 and a plurality of corresponding pairs of leads 32 remain within the spirit and scope of the present disclosure.

As described above, an exemplary way to form the partial magnetic loops $59_2$, $65_2$ is to create a pair of partial mechanical loops $60_1$, $60_2$. The partial mechanical loops 60, 66 of the connectors 30, 56, respectively, may be formed in a variety of ways. For purposes of brevity, the description below will be limited to that of the formation of the partial mechanical loops 60 of the connector 30. It will be appreciated, however, that the same description applies with equal weight to the formation of the partial mechanical loops 66 of the cable connector 56. Accordingly, while the description will not be repeated with respect to the partial mechanical loops 66, the description below applies to the partial mechanical loops 66 of the connector 56 with equal weight.

Figure 8A:
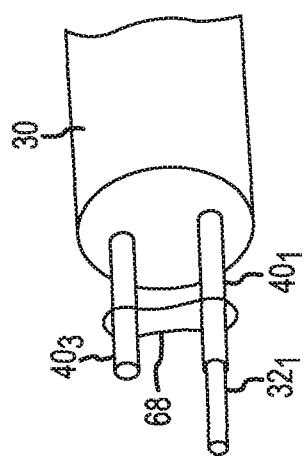
FIGS. 8a-8d are isometric views of a portion of an electromechanical connector, such as, for example, that depicted in FIG. 3a, illustrating alternate exemplary ways of creating partial loops between a pair of pins of the connector.
Figure 8B:
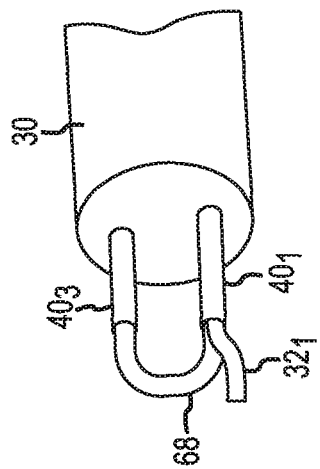

In an exemplary embodiment, the first and second electrical jumpers that comprise portions of respective partial mechanical loops 60 may comprise electrical conductor elements (e.g., jumper wire) connected between respective pairs of pins 40. For example, and as illustrated in FIG. 8a, a jumper 68 formed of an electrically conductive material may be connected between the ends of pins $40_1$, $40_3$ to form the partial mechanical loop $60_1$. In another exemplary embodiment, such as that illustrated in FIG. 8b, rather than the jumper 68 being connected between the ends of the pins $40_1$, $40_3$, it may be connected between the pins $40_1$, $40_3$ at a location between the ends of the pins and the base of the connector 30. In either embodiment, a second jumper 68 would be electrically connected between pins $40_2$, $40_4$ to form the partial mechanical loop $60_2$, however, for purposes of clarity and illustration, this arrangement is not depicted in FIG. 8a or 8b.

In another exemplary embodiment, the first and second electrical jumpers that comprise portions of respective partial mechanical loops 60 may comprise traces on a printed circuit board that is mounted on the body of the connector 30 (e.g., on the base of the connector 30 proximate the pins 40). More particularly, and as illustrated in FIG. 8c, a printed circuit board 70 having a plurality of through-holes $72_{1-N}$, each configured to receive a respective pin 40 of the connector 30, may be mounted onto the body of the connector 30. In such an embodiment, the through-holes $72_{1-N}$ of the circuit board 70 may be aligned with the pins 40 of the connector 30 and then slid on and mounted to the body of the connector 30. The circuit board 70 may be mounted to the body of the connector 30 using an adhesive, for example.

In the embodiment illustrated in FIG. 8c, the pins $40_1$, $40_3$ of the connector 30 are received by and disposed within the through-holes $72_1$, $72_3$. The through-holes $72_1$, $72_3$ each comprise a surface formed of electrically conductive material that is in contact with the pins $40_1$, $40_3$, respectively. In an exemplary embodiment, the pins 40 may be soldered to the conductive surfaces of the through-holes $72_{1-N}$. The electrically conductive surfaces of the through-holes $72_1$, $72_3$ are electrically connected to each other by an electrical trace $74_1$ on a first layer of the circuit board 70. The combination of the conductive surface of the through-holes $72_1$, $72_3$ and the trace $74_1$ form the partial mechanical loop $60_1$. In such an embodiment, the circuit board 70 comprises a second pair of through-holes $72_2$, $72_4$ and a second electrical trace $74_2$ disposed on a second layer of the circuit board 70 (shown in phantom lines to represent that the trace $74_2$ is disposed on a second layer of the circuit board 70) to form the second partial mechanical loop $60_2$ between the pins $40_2$, $40_4$. However, for purposes of clarity and illustration, this arrangement is not fully depicted in FIG. 8c.

In yet another exemplary embodiment, and similar to the embodiment described above and illustrated in FIG. 8c, the first and second electrical jumpers may also be formed by traces on a printed circuit board that is mounted on the body of the connector 30. However, in this embodiment, and with reference to FIG. 8d, rather than the leads 32 being electrically connected directly to the pins 40 of the connector 30, the leads 32 are connected to solder pads on the circuit board 70. Accordingly, the circuit board 70 effectively replaces the portions of the pins 40 extending outward from the body of the connector 30.

Figure 8D:
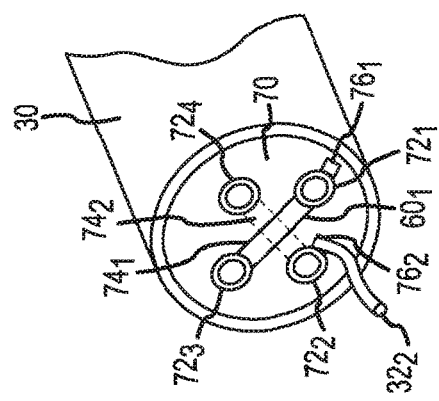
Figure 8C:
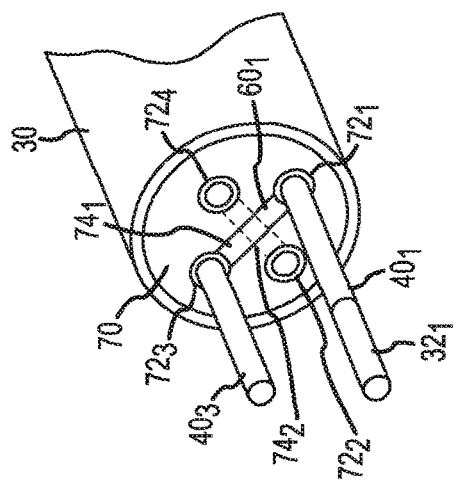

More particularly, and as illustrated in FIG. 8d, a printed circuit board 70 having a plurality of through-holes 72, each configured to receive a portion of a respective pin 40 of the connector 30, may be mounted onto the body of the connector 30. In such an embodiment, the through-holes 72 of the circuit board 70 may be aligned with the pins 40 of the connector 30 and then mounted to the body of the connector 30 using, for example, an adhesive. Portions of the pins $40_1$, $40_3$ of the connector 30 are received by and disposed within the through-holes $72_1$, $72_3$. The through-holes $72_1$, $72_3$ each comprise a surface formed of electrically conductive material that is in contact with the pins $40_1$, $40_3$, respectively. In an exemplary embodiment, the pins 40 may be soldered to the conductive surfaces of the through-holes $72_{1-N}$. In the embodiment illustrated in FIG. 8d, rather than connecting the leads 32 directly to the pins 40, the circuit board 70 has a plurality of solder or bond pads $76_{1-N}$ to which the leads 32 are electrically connected (e.g., soldered). More particularly, the circuit board 70 has a solder pad $76_1$ to which the lead $32_1$ is connected, and a solder pad $76_2$ to which the lead $32_2$ is connected. Each solder pad 76 is, in turn, electrically connected to the corresponding electrically conductive surface of a respective through-hole $72_{1-N}$. For example, the solder pad $76_1$ illustrated in FIG. 8d is electrically connected to the conductive surface of the through-hole $72_1$. Similarly, the solder pad $76_2$ is electrically connected to the conduction surface of the through-hole $72_2$. Accordingly, a lead 32 may be connected to a pin 40 of the connector 30 through a solder pad $76_{1-N}$ and an electrically conductive surface of a through-hole $72_{1-N}$ that is electrically connected to both the solder pad 76 and the pin 40.

As with the embodiment illustrated in FIG. 8c, in an embodiment such as that illustrated in FIG. 8d, the electrically conductive surfaces of the through-holes $72_1$, $72_3$ are electrically connected to each other by an electrical trace $74_1$ on a first layer of the circuit board 70. The combination of the conductive surface of the through-holes $72_1$, $72_3$ and the trace $74_1$ form the partial mechanical loop $60_1$. In such an embodiment, the circuit board 70 comprises a second pair of through-holes $72_2$, $72_4$ and a second electrical trace $74_2$ disposed on a second layer of the circuit board 70 (shown in phantom lines to represent that the electrical trace $74_2$ is disposed on a second layer of the circuit board 70) to form the second partial mechanical loop $60_2$ between the pins $40_2$, $40_4$. However, for purposes of clarity and illustration, this arrangement is not fully depicted in FIG. 8d.

Accordingly, it will be appreciated by those having ordinary skill in the art that the partial mechanical loops of the connectors of both the catheter and the cable configured to be mated therewith, may be formed in any number of ways, each of which remains within the spirit and scope of the present disclosure.

In addition to including partial magnetic loops 59, 65 in each connector 30, 56 that combine to form a pair of magnetic noise cancellation loops 54, 58, in an exemplary embodiment, one or both of the connectors 30, 56 may also be shielded. More particularly, a magnetic shield 77 (best shown in FIGS. 3a and 10a) formed of a material with high magnetic permeability may placed over the outer housing of one or both of the connectors 30, 56. More particularly, a magnetic shield formed of what is commonly known as a "mu metal" (e.g., a nickel-iron alloy) can be placed over the connectors 30, 56. The magnetic shield acts to effectively reduce the strength of the magnetic field to which the electrical connector is exposed.

As briefly described above, the system 10 may further comprise a cable (e.g., the cable 34 described above) that may be used to connect the catheter 12 with one or more other components of the system 10. In an exemplary embodiment, the catheter 12 and cable 34 may combine to form a medical device assembly, while in another exemplary embodiment, the cable 34 may be part of the component of the system 10 to which the catheter 12 is being connected.

Figure 9:
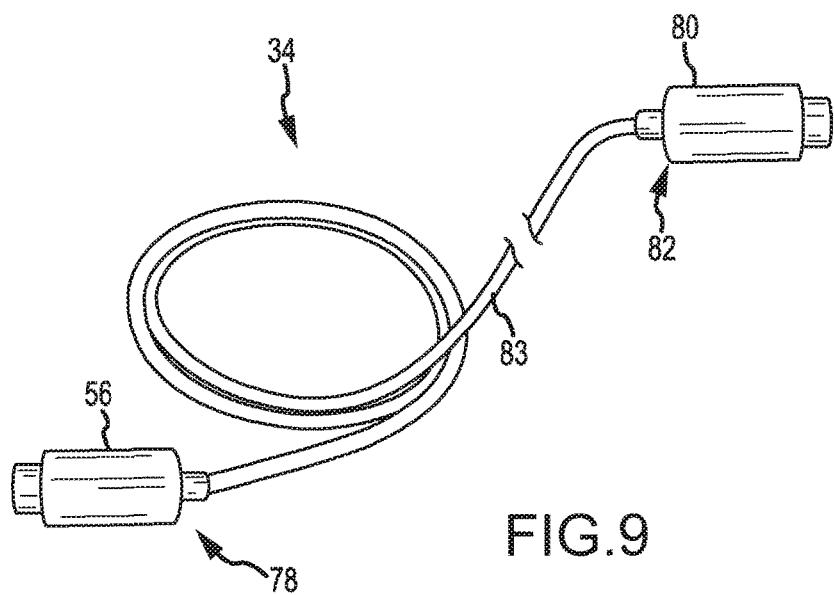
FIG. 9 is an isometric view of an exemplary electrical cable configured to electrically connect components of, for example, the system illustrated in FIG. 1.

In either instance, in an exemplary embodiment such as that illustrated in FIG. 9, the cable 34 comprises a first electromechanical connector, such as, for example, the connector 56 described above, at a first end 78 thereof, and a second electromechanical connector 80 disposed at a second end 82 thereof. The cable 34 further comprises a plurality of elongate electrical conductors $64_1$, $64_2$ (best shown in FIGS. 10a, 10b) extending between the first and second connectors 56, 80, and therefore, first and second ends 78, 82. In an exemplary embodiment wherein the catheter 12 comprises a single sensor 28, the cable 34 may comprise a single pair of electrical conductors 64. However, in an embodiment wherein the catheter 12 comprises a plurality of sensors 28, the cable 34 may comprise a pair of electrical conductors for each sensor 28 of the catheter 12.

As with the sensor leads 32 of the catheter 12, in order to account for the magnetic environment within which the cable 34 may be disposed as a result of its proximity to the magnetic field generated by the medical positioning system 14, each pair of electrical conductors 64 may be arranged in a twisted pair pattern along the length of the cable 34. For purposes of clarity and illustration, the description below will be with respect to an embodiment wherein the catheter 12 comprises a single sensor 28, and as such the cable 34 comprises a single pair of electrical conductors 64 (i.e., electrical conductors $64_1$, $64_2$). As is well known in the art, in addition to the electrical conductors 64 and the connectors 56, 80, the cable 34 may further comprise one or more insulation layers, as well as an outer sheath 83, surrounding the electrical conductors 64.

Figure 10:
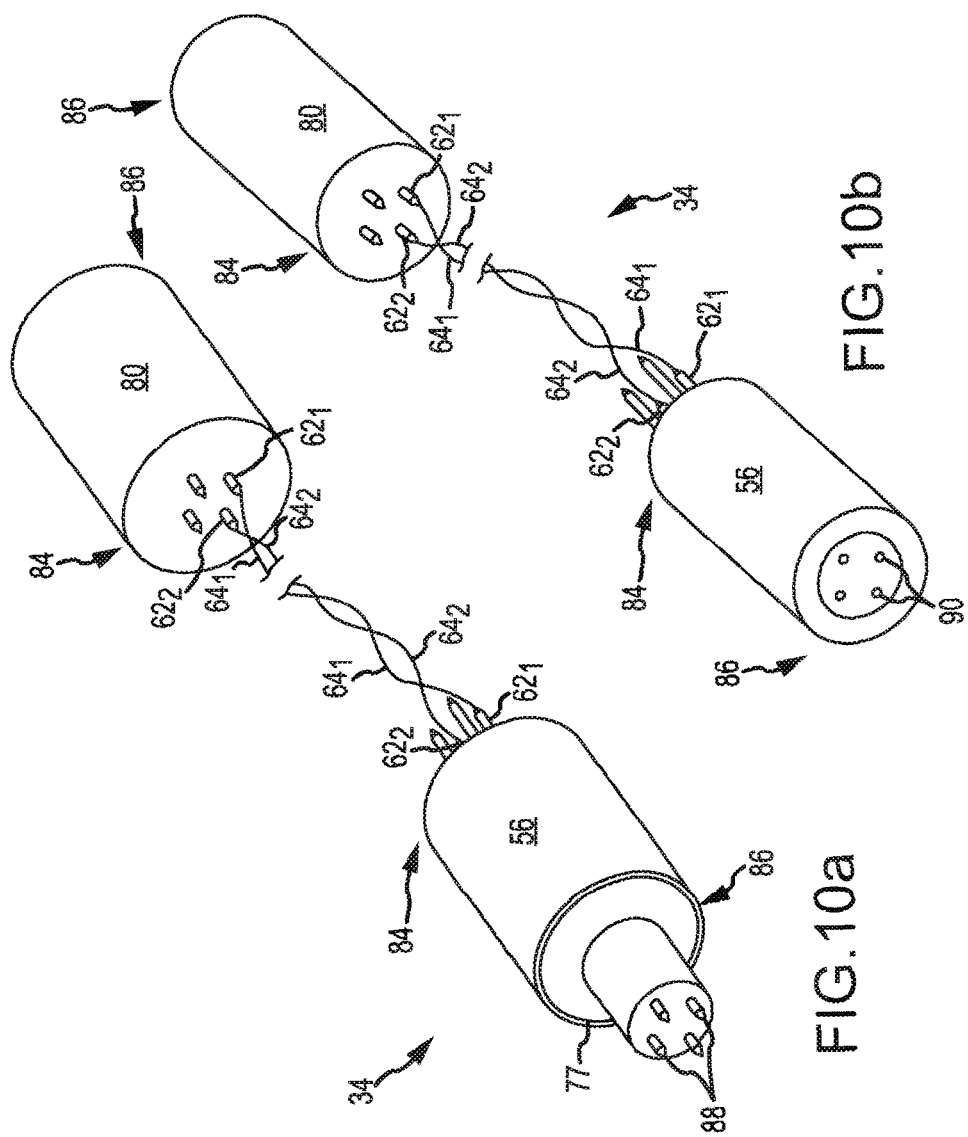
FIGS. 10a and 10b are isometric views of alternate exemplary embodiments of electromechanical connectors of the electrical cable illustrated in FIG. 9.

With reference to FIGS. 10a and 10b, and as described above with respect to the connector 30 of the catheter 12, each of the connectors 56, 80 comprises a first end 84 and a second end 86. The first end 84 of each connector 56, 80 has a plurality of pins 62, and each electrical conductor 64 of the cable 34 is electrically and mechanically connected or coupled to a respective one of the pins 62 of each connector 56, 80 (i.e., one end of each electrical conductor 64 is connected to a respective pin 62 of the connector 56, and the other end of each electrical conductor 64 is connected to a respective pin 62 of the connector 80). The second end 86 of each connector 56, 80 is configured to provide an interface between the cable 34 and the catheter 12, in the case of the cable connector 56, and the cable 34 and another component of the system 10, such as, for example, the medical positioning system 14 or a junction box, in the case of the connector 80.

In an exemplary embodiment, such as that illustrated in FIG. 10a, the second end 86 of one or both of the connectors 56, 80 may take the form of a male plug connector having a plurality of pins 88 that are electrically coupled to, or that comprise, the pins 62 disposed at the first end 84 of the connector 56, 80 (i.e., the pins 62 may extend through the first and second ends 84, 86 of the connectors 56, 80). In such an embodiment, the second end(s) 86 of the connector(s) 56, 80 are configured to be mated with a respective complementary female receptacle connector having a plurality of socket contacts configured to receive the pins 88 of the connector 56, 80. Alternatively, as illustrated in FIG. 10b, the second end 86 of one or both of the connector(s) 56, 80 may take the form of a female receptacle connector having a plurality of sockets 90 configured to receive a corresponding number of pins from a respective complementary male plug connector.

Accordingly, regardless of the particular form the connectors 56, 80 take, the cable 34 is configured to allow for the electrical connection of the catheter 12, and the sensor(s) 28 thereof, in particular, to one or more components of the system 10, such as, for example, the medical positioning system 14 or, as will be described in greater detail below, a junction box.

As described above, and as illustrated in FIG. 6, in exemplary embodiment, the connector 56 of the cable 34 comprises a pair of partial magnetic loops $65_1$, $65_2$ that are configured to combine with a pair of partial magnetic loops $59_1$, $59_2$ of the connector 30 to form a pair of complete magnetic loops 54, 58 when the connectors are mated. As described above, the purpose of these complete magnetic loops is to prevent, or at least substantially minimize, noise or interference generated in the connection arrangement or assembly of the complementary connectors. The description above with respect to the partial magnetic loops $65_1$, $65_2$ and the partial mechanical loops $66_1$, $66_2$ of the connector 56 applies here with equal weight and will not be repeated. Rather, the description above is incorporated here by reference.

As with the connector 56, the connector 80 also comprises a pair of partial magnetic loops $91_1$, $91_2$ that are configured to combine with a pair of partial magnetic loops of a complementary electromechanical connector of another component of the system 10, for example, to form a pair of complete magnetic loops when the connector 80 is mated therewith. As described above, the purpose of these complete magnetic loops is to prevent, or at least substantially minimize, noise or interface generated in the connection arrangement or assembly of the connector 80 and a complementary connector with which it is mated.

Figure 11:
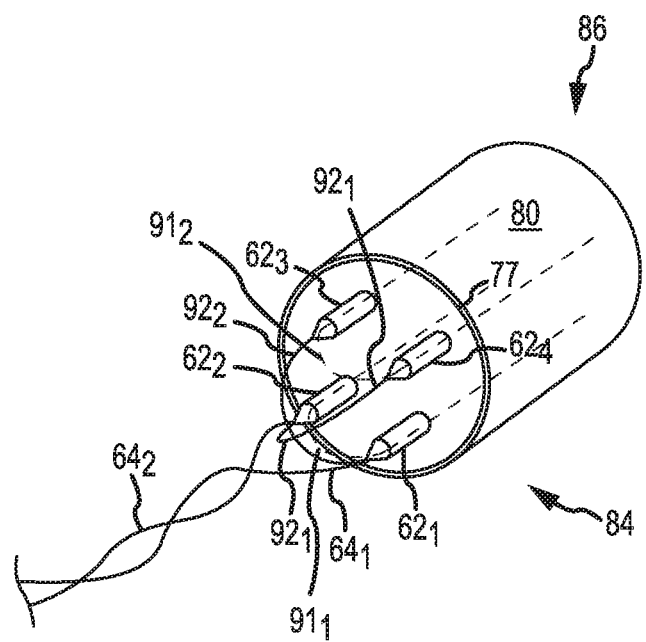
FIG. 11 is an isometric view of a portion of an electromechanical connector of the cable illustrated in FIG. 9, such as, for example, that depicted in FIG. 10a, illustrating a pair of partial magnetic loops, each formed between a pair of pins of the connector.

As illustrated in FIG. 11, the connector 80 comprises a pair of pins $62_1$, $62_2$ that are coupled to the ends of a pair of electrical conductors 64 (i.e., $64_1$, $64_2$) of the cable 34 (it will be appreciated that the other ends of the electrical conductors 64 are connected to pins 62 of the connector 56 disposed at the other end of the cable). The pins $62_1$, $62_2$ of the connector 80, along with an untwisted portion of the electrical conductors $64_1$, $64_2$ serve to form a first partial magnetic loop $91_1$ (represented by dotted or broken line in FIG. 11) that when combined with a partial magnetic loop of another component of the system 10 forms a first complete magnetic loop. As with the connectors described above, a second partial magnetic loop $91_2$ (also represented by dotted or broken line in FIG. 11) may be formed by creating a pair of mechanical partial loops $92_1$, $92_2$ between respective pairs of pins 62. The partial magnetic loop $91_2$ is configured to combine with a partial magnetic loop of another component of the system 10 to form a second complete magnetic loop that is substantially equal in area and opposite in orientation to the first complete magnetic loop that is formed, in part, by the partial magnetic loop $91_1$.

More particularly, to form a first partial mechanical loop $92_1$, the pin $62_1$ is electrically connected or jumped to another pin of the connector 80, namely, pin $62_3$, with a first electrical jumper. Similarly, to form a second partial mechanical loop $92_2$, the pin $62_2$ is electrically connected or jumped to another pin of the connector 80, namely, pin $62_4$, with a second electrical jumper. When the two partial mechanical loops $92_1$, $92_2$ are in place, they act to form or create the partial magnetic loop $91_2$ between the pins $62_3$, $62_4$ that is substantially parallel to the partial magnetic loop $91_1$ between the pins $62_1$, $62_2$.

As with the partial mechanical loops 66 of the connector 56, in an exemplary embodiment, the pins 62 of the connector 80 that are used to form the two partial mechanical loops $92_1$, $92_2$ are arranged in a square with each pin 62 comprising a vertex of the square, and with the pins 62 that are connected to each other to form a partial mechanical loop 92 being diagonal from each other. For example, in the embodiment illustrated in FIG. 11, the pins $62_1$-$62_4$ are arranged in a square, with pin $62_1$ and pin $62_3$, which form partial mechanical loop $92_1$, being diagonal from each other, and pin $62_2$ and pin $62_4$, which form partial mechanical loop $92_2$, also being diagonal from each other. Further, in an exemplary embodiment, the partial mechanical loops $92_1$, $92_2$ may be substantially the same size or length as the length of the untwisted portion of the pair of electrical conductors 64 that are connected to the pins 62 of the connector 80 (e.g., the loops $92_1$, $92_2$ may be substantially the same size as the untwisted portion of the electrical conductors $64_1$, $64_2$ proximate the connector 80). In order to reduce or limit the area of the loops created in the manner described herein, in an exemplary embodiment, the pins $62_1$-$62_4$ are arranged to be as close to each other as possible.

The partial mechanical loops $92_1$, $92_2$ of the connector 80 may be formed in a variety of ways. For example, and as with the partial mechanical loops 66 of the connector 56, the partial mechanical loops $92_1$, $92_2$ may be formed in the same manner as that described above with respect to the formation of the partial mechanical loops 60 of the connector 30. As such, the description above with respect to the formation of the partial mechanical loops 60 of the connector 30 applies here with equal force and, in the interest of brevity, will not be repeated. Rather the description set forth above is incorporated here by reference.

Accordingly, by arranging the electrical conductors 64 in a twisted pair arrangement and including a pair of partial magnetic loops $91_1$, $91_2$ in each connector 56, 80 of the cable 34, noise or interference caused by the exposure of the cable 34 to a magnetic field environment may prevented, or at least substantially reduced, thereby preventing, or at least substantially limiting, the introduction of errors in P&O determinations that are based on the signals generated by the sensor 28 and transmitted over the connectors 56, 80 and the electrical conductors 64 of the cable 34.

In addition to including partial magnetic loops in each connector 56, 80 that combine with partial magnetic loops of a complementary connector when mated therewith to form a pair of magnetic noise cancellation loops, in an exemplary embodiment, one or both of the connectors 56, 80 may also be shielded. More particularly, a magnetic shield 77 (best shown in FIGS. 10a and 11) formed of a material with high magnetic permeability may placed over the outer housing of one or both of the connectors 56, 80. More particularly, a magnetic shield formed of, for example, mu metal can be placed over the connectors 56, 80. The magnetic shield acts to effectively reduce the strength of the magnetic field to which the electrical connector is exposed.

As described above, the cable 34 is configured to electrically and mechanically connect the catheter 12, and the sensor 28 thereof, in particular, to one or more other components of the system 10. As also described above, the cable 34 includes an electromechanical connector 80 that is configured be mated with a complementary electromechanical connector of another component of the system 10. One such component is a junction box 94 that, as illustrated in the exemplary embodiment depicted in FIG. 4, is disposed between the catheter 12 and, for example, the medical positioning system 14.

The junction box 94 may serve a number of purposes. For example, in an exemplary embodiment, such as that illustrated in FIG. 4, the junction box 94 is configured to house an amplifier circuit for amplifying the signals generated by the sensors 28. In another exemplary embodiment, such as that illustrated in FIG. 12, the junction box 94 may be configured, at least in part, to consolidate a plurality of cables 34 corresponding to a plurality of catheters 12 into a single cable that is then routed to one or more other components of the system 10 (e.g., an amplifier, the medical positioning system 14, an ablation generator, a electrophysiology recording system, a tissue contact sensing system, etc.).

Figure 12:
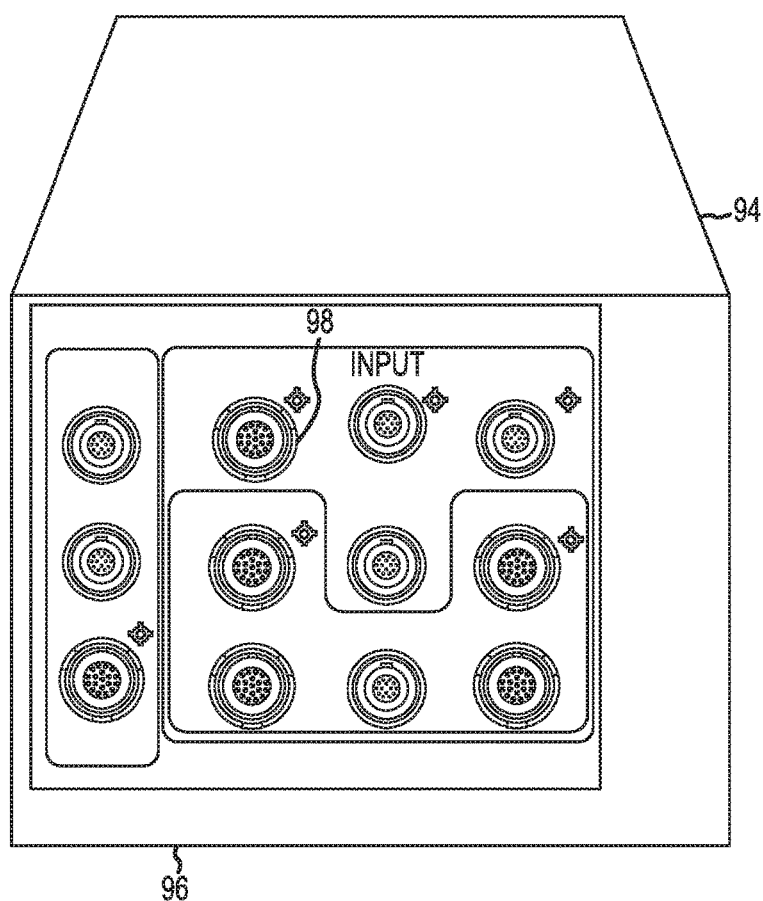
FIG. 12 is a perspective view of an exemplary junction box configured for use in the system illustrated in FIG. 1.

In any event, and with reference to FIG. 12, the junction box 94 comprises a housing 96 that is configured to house one or more components. The housing 96 may be constructed of a number of materials, such as, for example, plastic. Due to the proximity of the junction box to magnetic field generated by the medical positioning system 14, the junction box 94 may further include magnetic field shielding. For example, in an exemplary embodiment, the junction box 94 may be shielded by a material, such as, for example, mu metal, that is configured as a magnetic shield and acts to effectively eliminate or substantially reduce the strength of the magnetic field to which the components within the housing 94 are exposed.

The junction box 94 further comprises one or more input ports, each in the form of an electromechanical connector 98, disposed in a wall of the housing 96 that is/are configured to be mated with, for example, one or more respective complementary electromechanical connectors, such as, for example, the connector 80 of the cable 34. In an exemplary embodiment such as that illustrated in FIG. 13, and as will be described more fully below, a first end 100 of the connector 98 is disposed internal to the housing 96 and has a plurality of pins $102_{1-N}$. In an exemplary embodiment, two or more of the pins $102_{1-N}$ are electrically connected to a header 104 of a circuit board 106 disposed within the housing 96 by respective electrical conductors $108_{1-N}$ (e.g., wires $108_1$, $108_2$, $108_3$, $108_4$). A second end 110 of the connector 98 opposite the first end 100 is configured to be mated with, for example, one or more respective complementary electromechanical connectors, such as, for example, the connector 80 of the cable 34, and therefore, to provide an interface between the catheter 12, and the sensor (s) 28 thereof, in particular, and the junction box 94.

For example, in an exemplary embodiment, the second end 110 of the connector 98 may take the form of a male plug connector having a plurality of pins that are electrically coupled to, or that comprise, the pins 102 disposed at the first end 100 of the connector 98. In such an embodiment, the second end 110 of the connector 98 is configured to be mated with a complementary female receptacle connector of a cable, such as, for example, the connector 80 of the cable 34, having a plurality of socket contacts configured to receive the pins of the connector 98. Alternatively, the second end 110 of the connector 98 may take the form of a female receptacle connector having a plurality of sockets configured to receive a corresponding number of pins from a complementary male plug connector of a cable, such as, for example, the connector 80 of the cable 34.

For purposes of clarity and illustration, the description below will be limited to an embodiment wherein the junction box 94 has a single input port connector 98. For the same reasons, the description below will be further limited to an embodiment wherein the connector 98 is configured to accommodate a single-sensor catheter such that the first end 100 of the connector 98 comprises only four pins 102. It will be appreciated, however, that in other exemplary embodiments, the junction box 94 may comprise any number of input ports or connectors 98, as well as connectors 98 that are configured to accommodate catheters having any number of sensors mounted thereon. Therefore, embodiments wherein the junction box 94 comprises two or more connectors 98, or one or more connectors 98 that are each configured to accommodate a catheter having more than one sensor, remain within the spirit and scope of the present disclosure.

Because the junction box 94 may be disposed in relatively close proximity to the magnetic field generated by the medical positioning system 14, steps may be taken to prevent, or at least substantially minimize, noise or interference being introduced to the signals being transmitted from the catheter 12, and the sensor 28 thereof, in particular, through the junction box 94 from the exposure of the junction box 94 to a magnetic field environment.

For the same reasons described above with respect to the connector 30 of the catheter 12, one particular location in which such steps may be taken is at the connector 98 of the junction box 94. As described above, the connector 98 is configured to be mated with a complementary connector of a cable, such as, for example, the connector 80 of the cable 34. As also described above, the connector 80 includes a pair of partial magnetic loops 91 that when combined with corresponding partial magnetic loops of a complementary connector, form a pair of complete magnetic loops (i.e., magnetic field noise cancellation loops). Accordingly, in an exemplary embodiment, the connector 98 comprises a pair of partial magnetic loops $111_1$, $111_2$ that are complementary with the partial magnetic loops 91 of the connector 80, and therefore, are configured to form a pair of complete magnetic loops therewith when the connectors 80, 98 are mated.

Figure 13:
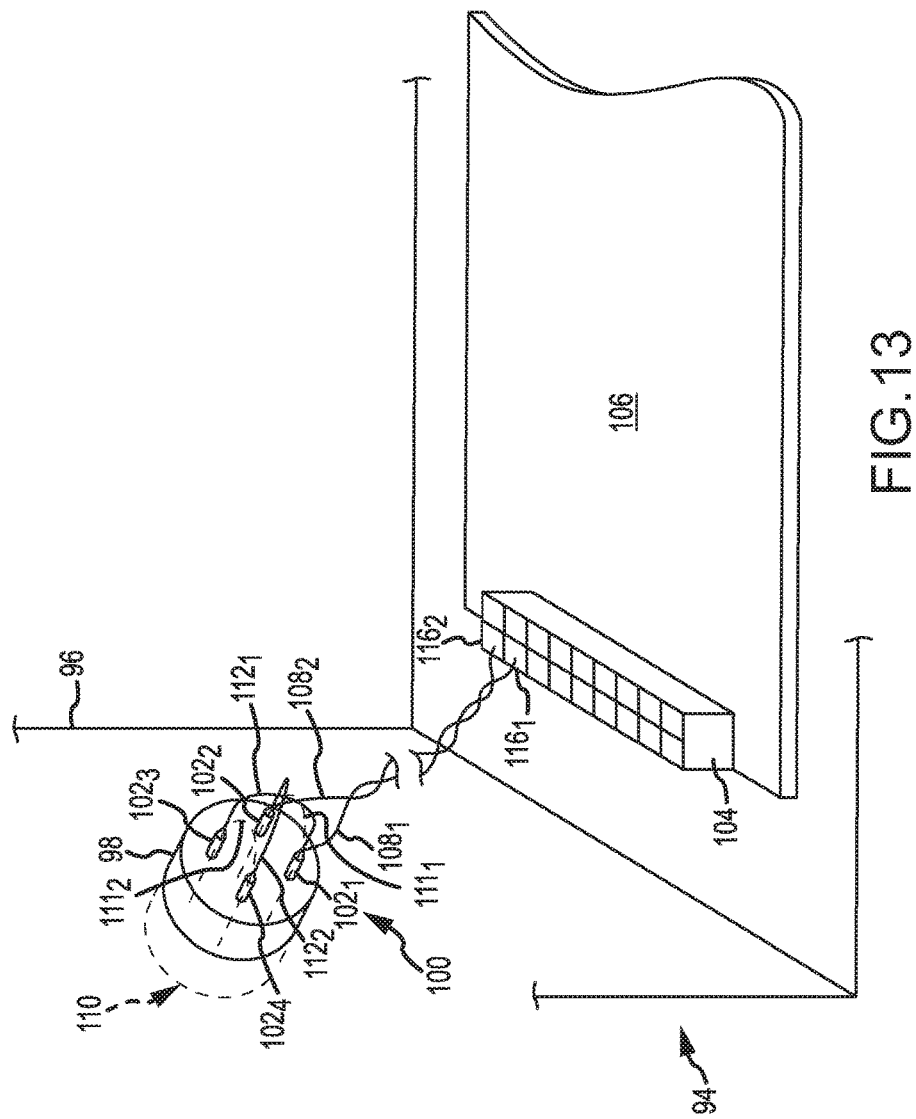
FIG. 13 is an isometric view of a portion of an exemplary embodiment of the junction box illustrated in FIG. 12.

Accordingly, as illustrated in FIG. 13, the connector 98 comprises a pair of pins $102_1$, $102_2$ that are configured to be electrically coupled with the corresponding pins $62_1$, $62_2$ of the connector 80, and therefore, the electrical conductors $64_1$, $64_2$ of the cable 34. In an exemplary embodiment, the pins $102_1$, $102_2$ are coupled to wires $108_1$, $108_2$, respectively, that are arranged in a twisted pair pattern between the connector 98 and the header 104. The pins $102_1$, $102_2$ along with an untwisted portion of the wires $108_1$, $108_2$ proximate the connector 98 serve to form a first partial magnetic loop $111_1$ (represented by dotted or broken line in FIG. 13) that when combined with the partial magnetic loop $91_1$ of the connector 80 when the connectors 80, 98 are coupled together, form a complete magnetic loop.

As with the connectors described above, a second partial magnetic loop $111_2$ (also represented by dotted or broken line in FIG. 13) may be formed between a respective pair of pins 102, namely, pins $102_3$, $102_4$. When the connectors 80, 98 are coupled together, the partial magnetic loop $91_2$ of the connector 80 is combined with the partial magnetic loop $111_2$ of the connector 98 to form a complete magnetic loop that is substantially equal in area and opposite in orientation to the complete magnetic loop that is formed, in part, by the partial magnetic loops $91_1$, $111_1$. In an exemplary embodiment, the partial magnetic loop $111_2$ may be formed by creating a pair of partial mechanical loops $112_1$, $112_2$ between respective pairs of pins 102.

More particularly, to form a first partial mechanical loop $112_1$, the pin $102_1$ is electrically connected or jumped to another pin 102 of the connector 98, namely, pin $102_3$, with a first electrical jumper. Similarly, to form a second partial mechanical loop $112_2$, the pin $102_2$ is electrically connected to another pin 102 of the connector 98, namely, pin $102_4$, with a second electrical jumper. When the two mechanical partial loops $112_1$, $112_2$ are in place, they act to form or create the partial magnetic loop $111_2$ between the pins $102_3$, $102_4$ that is substantially parallel to the partial magnetic loop $111_1$ between the pins $102_1$, $102_2$.

As with the partial mechanical loops 92 of the connector 80, in an exemplary embodiment, the pins 102 of the connector 98 that are used to form the two partial mechanical loops $112_1$, $112_2$ may be arranged in a square with each pin 102 comprising a vertex of the square, and with the pins 102 that are connected to each other to form a partial mechanical loop 112 being diagonal from each other. For example, in the embodiment illustrated in FIG. 13, the pins $102_1$-$102_4$ are arranged in a square, with pin $102_1$ and pin $102_3$, which form partial mechanical loop $112_1$, being diagonal from each other, and pin $102_2$ and pin $102_4$, which form partial mechanical loop $112_2$, also being diagonal from each other. Further, in order to reduce or limit the area of the loops created in the manner described herein, in an exemplary embodiment, the pins $102_1$-$102_4$ are arranged to be as close to each other as possible.

In order for the partial magnetic loops 91 of the connector 80 and the partial magnetic loops 111 of the connector 98 to combine to form a pair of complete magnetic loops, the pins 62 that form the partial magnetic loops 91 and the pins 102 that form the partial magnetic loops 111 may be connected to each other when the connectors 80, 98 are mated. More particularly, the pins of the respective connectors 80, 98 are arranged in manner that when the connectors are mated, the pin $62_1$ of the connector 80 is electrically connected to the pin $102_1$ of the connector 98, the pin $62_2$ is electrically connected to the pin $102_2$, the pin $62_3$ is electrically connected to the pin $102_3$, and the pin $62_4$ is electrically connected to the pin $102_4$.

The partial mechanical loops 112 of the connector 98 may be formed in a variety of ways. For example, and as with the partial mechanical loops 66, 92 of the connectors 56, 80, the partial mechanical loops 112 may be formed in the same manner as that described above with respect to the formation of the partial mechanical loops 60 of the connector 30. As such, the description above with respect to the formation of the partial mechanical loops 60 of the connector 30 applies here with equal force and, in the interest of brevity, will not be repeated. Rather the description set forth above is incorporated here by reference. In addition to including partial magnetic loops in connector 98 that combine with partial magnetic loops of a complementary connector when mated therewith to form a pair of magnetic noise cancellation loops, in an exemplary embodiment, the connector 98 may also be shielded. More particularly, a magnetic shield (not shown) formed of a material with high magnetic permeability may be placed over the outer housing of the connector 98. More particularly, a magnetic shield formed of, for example, mu metal can be placed over the connector 98. The magnetic shield acts to effectively reduce the strength of the magnetic field to which the electrical connector is exposed.

In another exemplary embodiment, rather than the partial magnetic loops 111 that combine with the partial magnetic loops 91 of the cable connector 80 being located in the connector 98 itself, the partial magnetic loops 111 may be formed elsewhere within the junction box 94 such as, for example, on the circuit board 106. In one such embodiment, each of the pins $102_1$-$102_4$ (as opposed to just the pin pins $102_1$, $102_2$ in the embodiment described above and illustrated in FIG. 13) may be connected to the header 104 of the circuit board 106 by a respective conductor or wire 108. The partial magnetic loops on the circuit board 106 may be formed in a number of ways.

Figure 14:
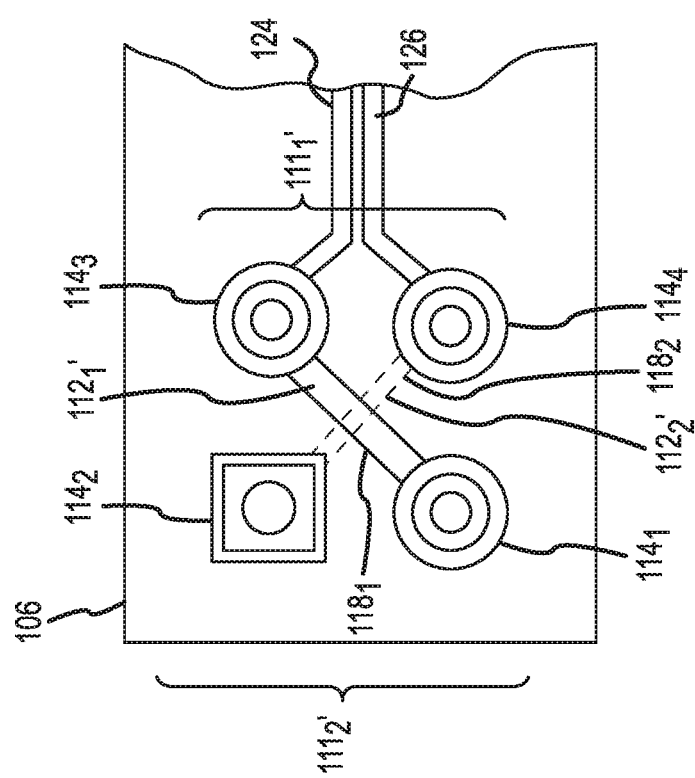
FIG. 14 is a plan view of an exemplary embodiment of a circuit board configured to be disposed within the junction box illustrated in FIG. 13.
Figure 15:
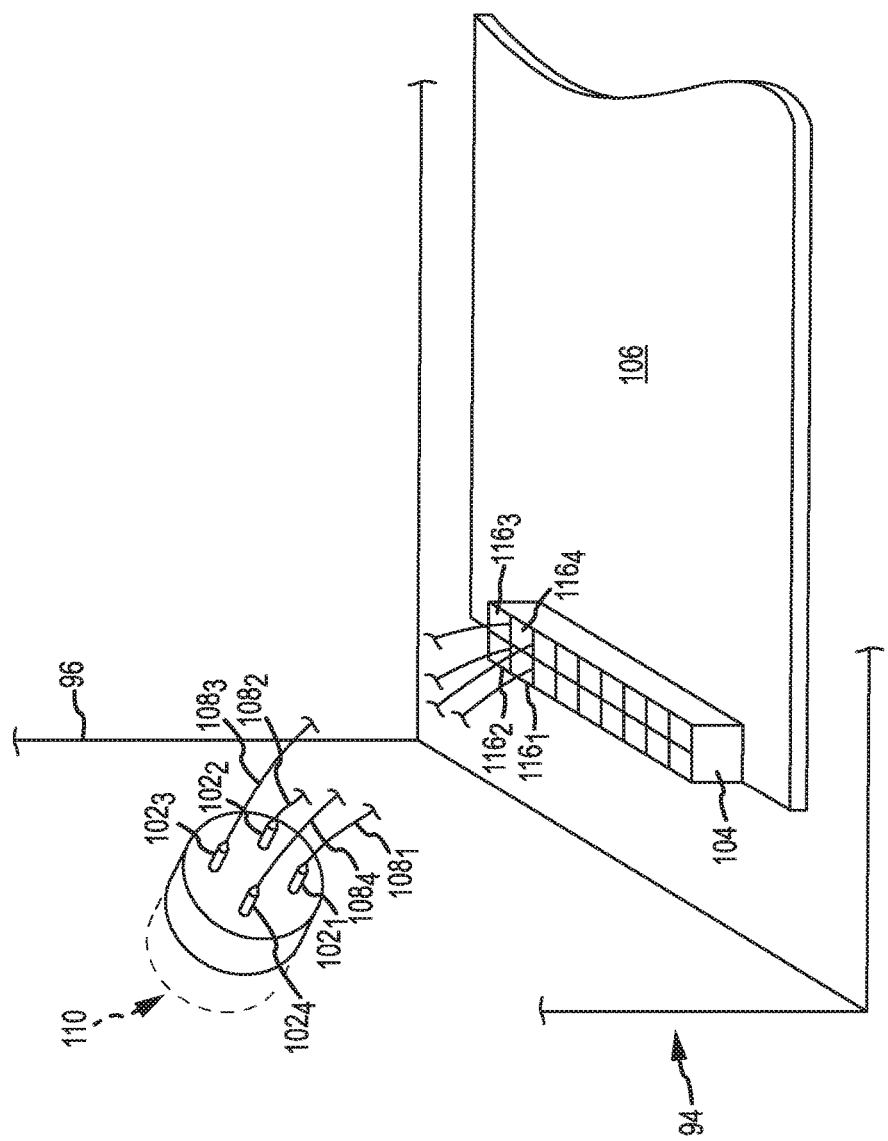
FIG. 15 is an isometric view of a portion of another exemplary embodiment of the junction box illustrated in FIG. 12.

More particularly, each of the pins $102_1$-$102_4$ of the connector 98 are electrically connected to a respective trace $114_1$-$114_4$ of the circuit board 106 through the combination of a respective wire 108 and the header 104 of the circuit board 106 (not shown in FIG. 14). For example, and as illustrated in FIG. 15, a wire $108_1$ is electrically connected between the pin $102_1$ and a socket $116_1$ of the header 104, which has a corresponding electrically conductive element disposed within the body of the header 104 that is configured to electrically connect the wire $108_1$ to the trace $114_1$ of the circuit board 106 (the trace $114_1$ is best shown in FIG. 14).

Similarly, wires $108_2$-$108_4$ are electrically connected between respective pins $102_2$-$102_4$ and sockets $116_2$-$116_4$ of the header 104, each socket $116_{1-N}$ having a corresponding electrically conductive element disposed within the body of the header 104 that is configured to electrically connect the respective wires $108_2$-$108_4$ to the traces $114_2$-$114_4$ of the circuit board 106. Accordingly, the wires 108 effectively extend the loops created by the partial magnetic loops 91 of the connector 80 down to the circuit board 106. It will be appreciated that in an exemplary embodiment, the wires 108 may be arranged in twisted pairs. For example, in one such embodiment, the wires $108_1$, $108_3$ may be arranged in a twisted pair pattern, and the wires $108_2$, $108_4$ may also be arranged in such a pattern. Alternatively, the wires 108 may not be arranged in twisted pairs.

With reference to FIG. 14, a first partial magnetic loop $111_1$' that will complete the second partial magnetic loop $91_2$ of the cable connector 80, is formed between the traces $114_3$ and $114_4$ of the circuit board 106. More particularly, each of these traces is electrically coupled to signal and return traces, respectively, on the circuit board 106. The combination of the arrangement of the signal and return traces proximate the traces $114_3$, $114_4$ and the traces $114_3$, $114_4$ themselves, forms the first partial magnetic loop $111_1$' between the traces $114_3$, $114_4$.

In an exemplary embodiment, a second partial magnetic loop $111_2$' that will complete the partial magnetic loop $91_1$ of the cable connector 80 may be formed by a pair of partial mechanical loops 112' disposed on the circuit board 106. More particularly, to form a first partial mechanical loop $112_1$', the trace $114_1$ is electrically connected to the trace $114_3$ by yet another trace (i.e., trace $118_1$) disposed on a first layer or top side of the circuit board 106. Similarly, to form a second partial mechanical loop $112_2$', the trace $114_2$ is electrically connected to the trace $114_4$ by yet still another trace (i.e., trace $118_2$, which is shown in phantom in FIG. 14 to indicate that it is on another layer or bottom side of the board 106 from trace $118_1$) that may be disposed on a second layer or bottom side of the circuit board 106. The two partial mechanical loops $112_1$', $112_2$' act to form or create the partial magnetic loop $111_2$' between the traces $114_1$, $114_2$. When the partial magnetic loops $91_1$, $111_2$' and $91_2$, $111_1$' are combined, they form a pair of complete magnetic noise cancellation loops that are substantially equal in area and opposite in orientation.

As described elsewhere above, in order to create partial magnetic loops that when combined with two other partial magnetic loops to form two complete magnetic loops that are both equal in area and opposite in orientation, the two partial mechanical loops of each of the connector 80 and the circuit board 106 may also be equal in area and opposite in orientation relative to each other. To that end, the electrical traces 114 of the circuit board 106 that are used to form the two partial magnetic loops 111' may be arranged in a square, with each trace 114 comprising a respective vertex of the square, and with the traces 114 that are connected to each other to form a partial mechanical loop 112' being diagonal from each other. For example, in the embodiment illustrated in FIG. 14, the traces $114_1$-$114_4$ are arranged in a square, with traces $114_1$, $114_3$, which form partial mechanical loop $112_1$', being diagonal from each other, and traces $114_2$, $114_4$, which form partial mechanical loop $112_2$', also being diagonal from each other.

In yet another exemplary embodiment, rather than the partial magnetic loops 111' disposed on the circuit board 106 being located proximate the header 104 thereof, the partial magnetic loops 111' are effectively formed and extend along the length of the circuit board 106. In such an embodiment, the partial magnetic loops 111' may terminate proximate an amplifier disposed on the circuit board 106, or an output port of the junction box 94.

Figure 16:
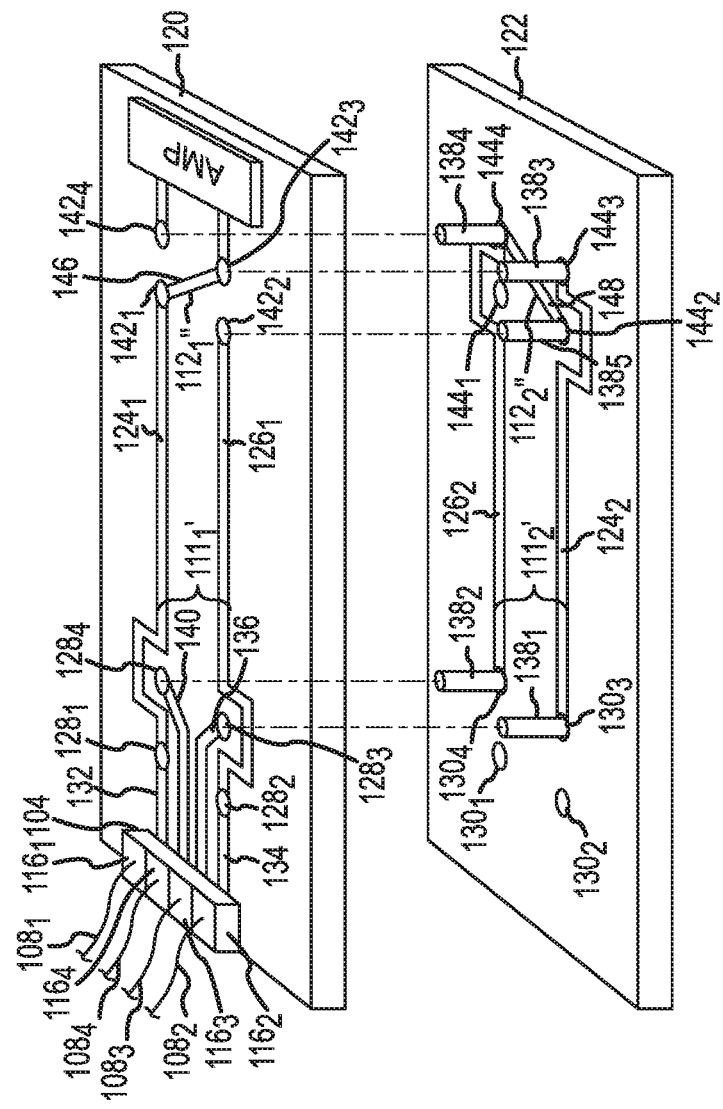
FIG. 16 is an isometric view of another exemplary embodiment of a circuit board configured to be disposed within the junction box illustrated in FIG. 13.

In such an embodiment, and with reference to FIG. 16, through a combination of the wires $108_1$-$108_4$ and corresponding sockets $116_1$-$116_4$ of the header 104 (and the electrically conductive elements thereof in particular), each of the pins $102_1$-$102_4$ of the connector 98 are electrically connected to either a signal trace or a return trace of the circuit board 106. In an exemplary embodiment, the wire pairs $108_1$, $108_3$ and $108_2$, $108_4$ may each be arranged in a twisted pair pattern between the pins 102 and the sockets 116, however, in other embodiments the wires 108 may not be so arranged, but rather may be arranged in a different manner.

With continued reference to FIG. 16, and as briefly described above, the circuit board 106 comprises both signal and return traces thereon. More particularly, in an exemplary embodiment, the circuit board 106 comprises a first layer 120 and a second layer 122 with each layer 120, 122 containing a signal trace 124 and a return trace 126 thereon. For example, the first layer 120 may comprise a first signal trace $124_1$ and a first return trace $126_1$ disposed thereon, while the second layer 122 may comprise a second signal trace $124_2$ and a second return trace $126_2$ disposed thereon.

As illustrated in FIG. 16, in at least one exemplary embodiment, the second return trace $126_2$ on the second layer 122 of the circuit board 106 is located directly below the first signal trace $124_1$ on the first layer 120 thereof, while the second signal trace $124_2$ of the second layer 122 of the circuit board 106 is located directly below the first return trace $126_1$ of the first layer 120 thereof. The signal and return traces 124, 126 on each layer 120, 122 of the circuit board 106 are arranged in this manner such that they are opposite (and, in one embodiment, exactly opposite) to each other so that any magnetic pickup on the board 106 between the two traces on the first layer 120 is equal and opposite of the magnetic pickup between the two traces on the second layer 122. In other words the signal and return traces $124_1$, $126_1$ on the first layer 120 form a first partial magnetic loop $111_1''$ that combines with the partial magnetic loop $91_1$ of the connector 80 to form a first complete magnetic loop. Similarly, the signal and return traces $124_2$, $126_2$ on the second layer 122 form a second partial magnetic loop $111_2''$ that combines with the partial magnetic loop $91_2$ of the connector 80 to form a second complete magnetic loop. The complete magnetic loops formed by the partial magnetic loops $91_1$, $111_1''$ and $91_2$ and $111_2''$, respectively, are substantially equal in area and opposite in orientation to each other to cancel out currents induced therein as a result of magnetic pickup.

In at least one exemplary embodiment, the partial magnetic loops $111_1''$, $111_2''$ may be formed as follows. As briefly described above, each of the pins $102_1$-$102_4$ of the connector 98 are connected to one of the signal or return traces 124, 126. More specifically, in an embodiment such as that illustrated in FIG. 16, the first layer 120 of the circuit board 106 comprises a first set of four through-holes $128_1$-$128_4$ arranged, for example, in a square, and the second layer 122 also comprises a first set of four through-holes $130_1$-$130_4$ arranged, for example, in a square, and that are aligned (and, in one embodiment, exactly aligned) with the first set of through-holes $128_1$-$128_4$ of the first layer 120. In the illustrated embodiment, these first sets of through-holes of each layer 120, 122 of the circuit board 106 are disposed at or near a first end of the circuit board 106 proximate the header 104 thereof.

As illustrated in FIG. 16, in an exemplary embodiment, an electrically conductive surface of the first through-hole $128_1$ of the first layer 120 is electrically connected to an electrically conductive element of the socket $116_1$ of the header 104 to which the pin $102_1$ of the connector 98 is connected via the wire $108_1$. In an exemplary embodiment, the electrical connection between the electrically conductive surface of the first through-hole $128_1$ and the electrically conductive element of the socket $116_1$ is made through a first trace 132 on the circuit board 106. As illustrated in FIG. 16, the first signal trace $124_1$ is also electrically connected to the electrically conductive surface of the first through-hole $128_1$. Accordingly, through the combination of the wire $108_1$, the header socket $116_1$, and the electrically conductive surface of the through-hole $128_1$, the pin $102_1$ is electrically connected to the first signal trace $124_1$.

Similarly, in the illustrated embodiment, an electrically conductive surface of the second through-hole $128_2$ of the first layer 120 is electrically connected to an electrically conductive element of the socket $116_2$ of the header 104 to which the pin $102_2$ of the connector 98 is connected via the wire $108_2$. In an exemplary embodiment, the electrical connection between the electrically conductive surface of the second through-hole $128_2$ and the electrically conductive element of the socket $116_2$ is made through a second trace 134 on the circuit board 106. As illustrated in FIG. 16, the first return trace $126_1$ is also electrically connected to the electrically conductive surface of the second through-hole $128_2$. Accordingly, through the combination of the wire $108_2$, the header socket $116_2$, and the electrically conductive surface of the through-hole $128_2$, the pin $102_2$ is electrically connected to the first return trace $126_1$.

With continued reference to FIG. 16, in an exemplary embodiment, an electrically conductive surface the third through-hole $128_3$ of the first layer 120 is electrically connected to an electrically conductive element of the socket $116_3$ of the header 104 to which the pin $102_3$ of the connector 98 is connected with the wire $108_3$. In an exemplary embodiment, the electrical connection between the electrically conductive surface of the third through-hole $128_3$ and the electrically conductive element of the socket $116_3$ is made through a third trace 136 on the circuit board 106. As illustrated in FIG. 16, in an exemplary embodiment, an electrically conductive pin $138_1$ is disposed within and extends between each of the third through-hole $128_3$ of the first layer 120, and the third through-hole $130_3$ of the second layer 122. The pin $138_1$ serves to electrically connect the electrically conductive surfaces of the through-holes $128_3$, $130_3$. The electrically conductive surface of the third through-hole $130_3$ of the second layer 122 is electrically connected to the second signal trace $124_2$ of the second layer 122. Accordingly, through the combination of the wire $108_3$, the header socket $116_3$, the third through-hole $128_3$ of the first layer 120, the pin $138_1$, and the third through hole $130_3$ of the second layer 122, the pin $102_3$ is electrically connected to the second signal trace $124_2$.

Finally, in the illustrated embodiment, an electrically conductive surface of the fourth through-hole $128_4$ of the first layer 120 is electrically connected to an electrically conductive element of the socket $116_4$ of the header 104 to which the pin $102_4$ of the connector 98 is connected via the wire $108_4$. In an exemplary embodiment, the electrical connection between the electrically conductive surface of the fourth through-hole $128_4$ and the electrically conductive element of the socket $116_4$ is made through a fourth trace 140 on the circuit board 106. As illustrated in FIG. 16, in an exemplary embodiment, an electrically conductive pin $138_2$ is disposed within and extends between each of the fourth through-hole $128_4$ of the first layer 120, and the second through-hole $130_4$ of the second layer 122. The pin $138_2$ serves to electrically connect the electrically conductive surfaces of the through-holes $128_4$, $130_4$. The electrically conductive surface of the fourth through-hole $130_4$ of the second layer 122 is electrically connected to the second return trace $126_2$ of the second layer 122. Accordingly, through the combination of the wire $108_4$, the header socket $116_4$, the fourth through-hole $128_4$ of the first layer 120, the pin $138_2$, and the fourth through hole $130_4$ of the second layer 122, the pin $102_4$ is electrically connected to the second return trace $126_2$.

As illustrated in FIG. 16, in at least one exemplary embodiment, the first layer 120 of the circuit board 106 further comprises a second set of four through-holes $142_1$-$142_4$ arranged, for example, in a square, and the second layer 122 also comprises a second set of four through-holes $144_1$-$144_4$ arranged, for example, in a square, and that are aligned (and, in one embodiment, exactly aligned) with the second set of through-holes $142_1$-$142_4$ of the first layer 120. In the illustrated embodiment, these second sets of through-holes of each layer 120, 122 of the circuit board 106 are disposed at or near a second end of the circuit board 106 opposite the first end thereof at which the first sets of through-holes are disposed.

In the illustrated embodiment, an electrically conductive surface of the first through-hole $142_1$ of the first layer 120 is electrically connected to the first signal trace $124_1$. As illustrated in FIG. 16, the third through-hole $142_3$ of the first layer 120 is disposed diagonal from the first though-hole $142_1$ and has an electrically conductive surface that is electrically connected to that of the first though-hole $142_1$ by way of a trace 146 on the first layer 120 of the circuit board 106. In an exemplary embodiment, an electrically conductive pin $138_3$ is disposed within and extends between each of the third through-hole $142_3$ of the first layer 120 and the third through-hole $144_3$ of the second layer 122. The pin $138_3$ serves to electrically connect the electrically conductive surfaces of the through-holes $142_3$, $144_3$. As illustrated in FIG. 16, the electrically conductive surface of the third through-hole $144_3$ of the second layer 122 is electrically connected to the second signal trace $124_2$ disposed on the second layer 122. It will be appreciated that the electrically conductive surface of the third through-hole $142_3$ of the first layer 120 may be further electrically connected to, for example, an amplifier or an output port of the junction box 94 to allow for the further communication of the signal transmitted over the signal traces $124_1$, $124_2$ of the circuit board 106.

As a result of this arrangement, a first partial mechanical loop $112_1''$ is formed between the first and second layers 120, 122 of the circuit board 106, and the first and second signal traces $124_1$, $124_2$ thereof, in particular.

Similarly, as illustrated in FIG. 16, an electrically conductive surface of the fourth through-hole $144_4$ of the second layer 122 is electrically connected to the second return trace $126_2$ of the second layer 122. The second through-hole $144_2$ of the second layer 122 is disposed diagonally from the fourth through-hole $144_4$ of the second layer 122 and has an electrically conductive surface that is electrically connected to that of the fourth through-hole $144_4$ by way of a trace 148 on the second layer 122 of the circuit board 106. In an exemplary embodiment, an electrically conductive pin $138_4$ is disposed within and extends between each of the fourth through-hole $144_4$ of the second layer 122 and the fourth through-hole $142_4$ of the first layer 120. The pin $138_4$ serves to electrically connect the electrically conductive surfaces of the through-holes $142_4$, $144_4$.

In an exemplary embodiment, an electrically conductive pin $138_5$ is also disposed within and extends between each of the second through-hole $144_2$ of the second layer 122 and the second through-hole $142_2$ of the first layer 120. The pin $138_5$ serves to electrically connect the electrically conductive surfaces of the through-holes $142_2$, $144_2$. As illustrated in FIG. 16, the electrically conductive surface of the second through-hole $142_2$ of the first layer 120 is electrically connected to the first return trace $126_1$ that is disposed on the first layer 120. It will be appreciated that the electrically conductive surface of the fourth through-hole $142_4$ of the first layer 120 may be further electrically connected to, for example, an amplifier or an output port of the junction box 94 to allow for the extension of the return path from the circuit board 106.

As a result of the above-described arrangement, a second partial mechanical loop $112_2''$ is formed between the first and second layers 120, 122 of the circuit board 106, and the first and second return traces $126_1$, $126_2$ thereof, in particular.

The combination of the first and second partial mechanical loops $112_1''$ and $112_2''$ result in the formation of the first partial magnetic loop $111_1''$ on the first layer 120 of the circuit board 106 between the first signal and return traces $124_1$, $126_1$, and the formation of the second partial magnetic loop $111_2''$ on the second layer 122 of the circuit board 106 between the second signal and return traces $124_2$, $126_2$. The partial magnetic loop $111_1''$ combines with the partial magnetic loop $91_1$ of the connector 80 to form a first complete magnetic loop, while the partial magnetic loop $111_2''$ combines with the partial magnetic loop $91_2$ to form a second complete magnetic loop. As described above, the first and second complete magnetic loops are both substantially equal in area and opposite in orientation so as to cancel out any current induced therein as a result of magnetic pickup.

Accordingly, it will be appreciated by those having ordinary skill in the art that any number of arrangements can be implemented by which complete magnetic loops are formed between the partial magnetic loops of the cable connector 80 and partial magnetic loops disposed either within the connector 98 of the junction box 94 or within the junction box 94 itself, each of which remains within the spirit and scope of the present disclosure.

The description has thus far been primarily with respect to the prevention of noise or interference at the connection points between the catheter 12 and the cable 34, and the cable 34 and the junction box 94. In certain instances, such as, for example, when the junction box 94 is not shielded, there are other locations within the junction box 94 at which steps may be taken to prevent the introduction of noise or interference from the magnetic field environment. One such location is the area between the pins 102 of the junction box connector 98 and the circuit board 106 disposed within the junction box 94.

More particularly, and as described above, some or all of the pins 102 are electrically connected to the header 104 of the circuit board 106 by electrical conductors or wires 108. In general terms, these wires 108 serve to connect the sensor 28 to the circuit board 106. More specifically, the leads $32_1$, $32_2$ of the sensor 28 are connected to the electrical conductors $64_1$, $64_2$ of the cable 34 through the connection arrangement of the catheter connector 30 and a cable connector 56. The electrical conductors $64_1$, $64_2$ are, in turn, connected to the wires $108_1$, $108_2$, through the connection arrangement of the cable connector 80 and the junction box connector 98. The wires 108$_1$, 108$_2$ are then connected to the circuit board 106 through the header 104.

Due to the length of the wires 108, it is possible that they may act as a magnetic pickup, resulting in noise or interference to the signal generated by the sensor 28 and transmitted over the wires 108. As illustrated in FIG. 13, and as with the leads 32$_1$, 32$_2$ of the sensor 28 and the electrical conductors 64$_1$, 64$_2$ of the cable 34, one way to account for this is to arrange the wires 108 in a twisted pair pattern along the length of the wires 108 between the pins 102 and the header 104.

While this twisted pair arrangement of the wires 108 addresses the potential issue in the area between the pins 102 and the header 104, another area that may be susceptible to the generation of noise or interference as a result of the magnetic field environment is the area within the header 104 itself. More particularly, the combination of the untwisted portion of the wires 108 that is required to connect the wires 108 to the header 104 and the electrically conductive elements between the termination points of the wires 108 and the connection of the header 104 to traces on the circuit board 106 may create a magnetic loop that can act as a magnetic pickup.

To account for this, and similar to the connectors 30, 56, 80, 98 above, a second magnetic loop is formed that is substantially equal in area and opposite in orientation to the magnetic loop formed by between the electrically conductive elements of the header 104. As such, when the header 104 is subjected or exposed to a magnetic field, the currents induced in the two loops will be equal but opposite, thereby resulting in the currents offsetting each other. Thus, interference to the signals generated by the sensor 28 and transmitted through the header 104 is prevented, or at least substantially minimized.

Figure 17:
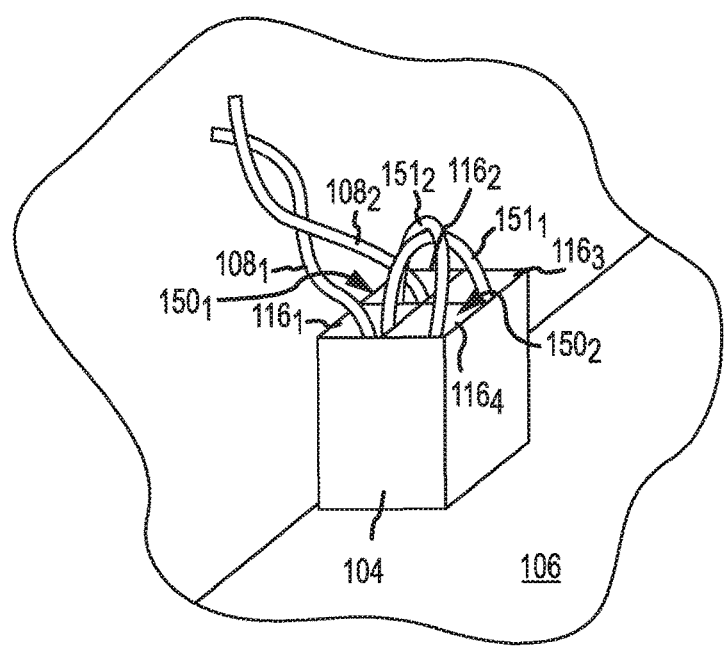
FIG. 17 is an enlarged isometric view of a portion of an exemplary circuit board disposed within the junction box illustrated in FIG. 13.

With reference to FIG. 17, to form the pair of complete magnetic loops, the top side of the header 104 at which the wires 108 terminate, and the circuit board 106 to which the header 104 is connected, each comprise a pair of partial magnetic loops (i.e., partial magnetic loops 150$_{1-2}$, 152$_{1-2}$, respectively) that combine to form the pair of complete magnetic loops.

With respect to the partial magnetic loops 150 of the header 104, each partial magnetic loop 150 comprises a pair of electrically conductive elements of the header 104, More particularly, and in an exemplary embodiment, one partial magnetic loop (referred to as "partial magnetic loop 150$_1$" below) is formed by the untwisted portion of the wires 108$_1$, 108$_2$ and the electrically conductive elements of the sockets 116$_1$, 116$_2$ of the header 104 to which the wires 108$_1$, 108$_2$ are electrically connected. As such, the partial magnetic loop 150$_1$ is formed between the electrically conductive elements of the sockets 116$_1$, 116$_2$. In an exemplary embodiment, the second partial magnetic loop (referred to as "partial loop 150$_2$" below) may be formed by creating a pair of mechanical partial loops 151$_1$, 151$_2$ between respective pairs of electrically conductive elements of sockets 116 of the header 104.

More particularly, each of the partial mechanical loops 151$_1$, 151$_2$ comprises a pair of electrically conductive elements of sockets of the header 104, with one electrically conductive element of each pair being connected to a wire 108. For example, in the embodiment illustrated in FIG. 17, the wires 108$_1$, 108$_2$ are electrically connected to the electrically conductive elements of the sockets 116$_1$, 116$_2$, respectively of the header 104. To form a first partial mechanical loop 151$_1$, the electrically conductive element of the socket 116$_1$ is electrically connected or jumped to the electrically conductive element of another socket 116, namely, socket 116$_3$, with a first electrical jumper. Similarly, to form a second partial mechanical loop 151$_2$, the electrically conductive element of the socket 116$_2$ is electrically connected or jumped to the electrically conductive element of another socket 116 of the header 104, namely, the electrically conductive element of the socket 116$_4$, with a second electrical jumper. When the two partial mechanical loops are in place, they act to form or create a second partial magnetic loop 150$_2$ between the electrically conductive elements of the sockets 116$_3$, 116$_4$ that is substantially parallel to the partial magnetic loop 150$_1$ between the electrically conductive elements of the sockets 116$_1$, 116$_2$.

In order to create partial magnetic loops that when combined with two other partial magnetic loops to form two complete magnetic loops that are both equal in area and opposite in orientation, the two partial magnetic loops of each of the header 104 and the circuit board 106 may also be equal in area and opposite in orientation relative to each other. To that end, in an exemplary embodiment, the electrically conductive elements, and therefore, the sockets 116 corresponding thereto, that form the two partial magnetic loops 150 of the header 104 may be arranged in a square with each electrically conductive element comprising a vertex of the square, and with the conductive elements and sockets 116 that are connected to each other to form a partial mechanical loop 151 being diagonal from each other. For example, in the embodiment illustrated in FIG. 17, the sockets 116$_1$-116$_4$ are arranged in a square, with socket 116$_1$ and socket 116$_3$, which form partial mechanical loop 151$_1$, being diagonal from each other, and socket 116$_2$ and socket 116$_4$, which form partial mechanical loop 151$_2$, also being diagonal from each other. Further, in an exemplary embodiment, the partial mechanical loops 151$_1$, 151$_2$ may be substantially the same size or length as the length of the untwisted portion of the wires 108 that are connected to the header 104 (e.g., the partial loops 151$_1$, 151$_2$ may be substantially the same size as the untwisted portion of the wires 108$_1$, 108$_2$ proximate the header 104).

As briefly described above, the partial magnetic loops 150 of the header 104 are configured to combine with a pair of partial magnetic loops 152 disposed on the circuit board 106 to form two complete magnetic loops. The partial magnetic loops 152 in the circuit board 106 may be formed in a number of ways.

Figure 18:
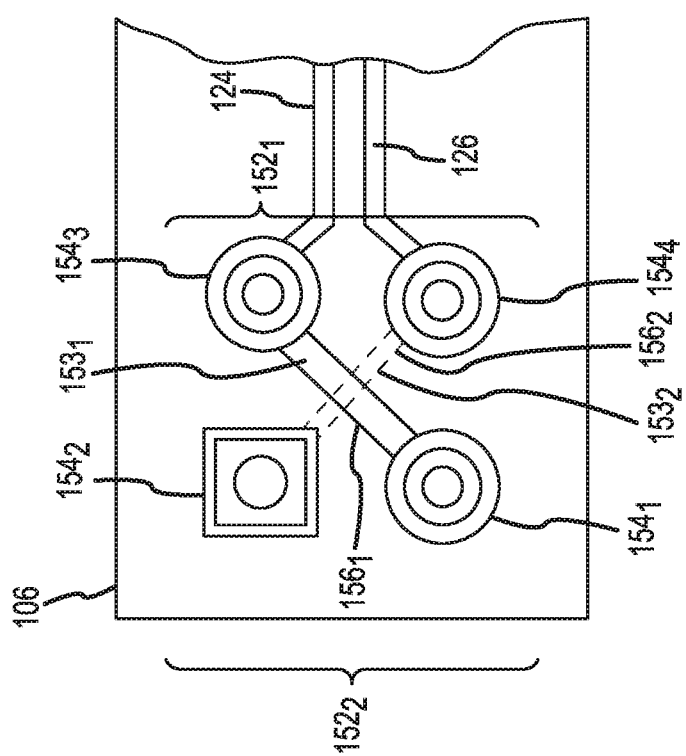
FIG. 18 is a plan view of a portion of the circuit board illustrated in FIG. 17.

More particularly, and with reference to FIG. 18, each of the electrically conductive elements of the header 104 corresponding to the sockets 116$_1$-116$_4$ thereof are electrically connected to a respective trace 154$_{1-N}$ on the circuit board 106. For example, the electrically conductive element corresponding to the socket 116$_1$, and therefore, wire 108$_1$ connected between the connector 98 and header 104, is coupled to a trace 154$_1$, and the conductive element corresponding to the socket 116$_2$, and therefore, the wire 108$_2$ connected between the connector 98 and the header 104, is coupled to a trace 154$_2$. Similarly, the conductive elements corresponding to the sockets 116$_3$, 116$_4$ are electrically connected to traces 154$_3$, 154$_4$, respectively.

With continued reference to FIG. 18, a first partial magnetic loop 152$_1$ that will complete the second partial magnetic loop 150$_2$ of the header 104, is formed between the traces 154$_3$ and 154$_4$ of the circuit board 106. More particularly, each of these traces is electrically coupled to a respective one a signal trace 124 and a return trace 126 on the circuit board 106. The combination of the arrangement of the signal and return traces 124, 126 proximate traces 154$_3$, $154_4$ and the traces $154_3$, $154_4$ themselves, forms the first partial magnetic loop $152_1$ between the traces $154_3$, $154_4$.

In an exemplary embodiment, a second partial magnetic loop $152_2$ that will complete the partial magnetic loop $150_1$ of the header 104 may be formed by a pair of partial mechanical loops $153_1$, $153_2$ disposed on the circuit board 106. More particularly, to form a first partial mechanical loop $153_1$, the trace $154_1$ is electrically to the trace $154_3$ by yet another trace (i.e., trace $156_1$) disposed on a first layer or the top side of the circuit board 106. Similarly, to form a second partial mechanical loop $153_2$, the trace $154_2$ is electrically connected to the trace $154_4$ by yet still another trace (i.e., trace $156_2$, which is shown in phantom in FIG. 18 to indicate that it is disposed on another layer or bottom side of the circuit board 106 from trace $156_1$) that may be disposed on a second layer or the bottom side of the circuit board 106. The two partial mechanical loops $153_1$, $153_2$ act to form or create the partial magnetic loop $152_2$ between the traces $154_1$, $154_2$. When the partial magnetic loops $150_1$, $152_2$ and $150_2$, $152_1$ are combined, they form a pair of complete magnetic noise cancellation loops that are substantially equal in area and opposite in orientation.

As described elsewhere above, in order to create partial magnetic loops that when combined with two other partial magnetic loops to form two complete magnetic loops that are both equal in area and opposite in orientation, the two partial magnetic loops of each of the header 104 and the circuit board 106 may also be equal in area and opposite in orientation relative to each other. To that end, in an exemplary embodiment, electrical traces $154_1$-$154_4$ of the circuit board 106 used to form the two partial magnetic loops $152_1$, $152_2$ of the circuit board 106 may be arranged in a square, with each trace $154_{1-N}$ comprising a respective vertex of the square, and with the traces $154_{1-N}$ that are connected to each other to form a partial mechanical loop $153_{1-N}$ being diagonal from each other. For example, in the embodiment illustrated in FIG. 18, the traces $154_1$-$154_4$ are arranged in a square, with traces $154_1$, $154_3$, which form partial mechanical loop $153_1$, being diagonal from each other, and traces $154_2$, $154_4$, which form partial mechanical loop $153_2$, also being diagonal from each other.

Accordingly, by forming two complete magnetic loops through the header 104 with a pair of partial magnetic loops disposed on both the header 104 and the circuit board 106, interference or noise to signals flowing through the header caused by a magnetic field environment can be prevented, or at least substantially minimized.

In certain embodiments, such as that wherein the junction box 94 is subjected or exposed to a magnetic field and the housing 96 thereof is not sufficiently shielded from magnetic fields, another area at which steps may need to be taken to prevent the introduction of noise or interference from the magnetic field environment is the circuit board 106 itself. More particularly, the signal and return traces 124, 126 of the circuit board 106 that are electrically connected to the leads 32 of the sensor 28 through, as described above, the various connectors, cables, and conductors, may create a loop on the circuit board 106 that can act as a magnetic pickup. One way to account for this, and as illustrated in FIGS. 14 and 18, is to arrange the traces 124, 126 using a differential pair routing technique. Arranging the traces 124, 126 as a differential pair on a single layer of the circuit board 106 and as close together as possible results in the differential pair effectively acting as a twisted pair of wires, and as such, serves to prevent magnetic pickup therein.

Figure 19:
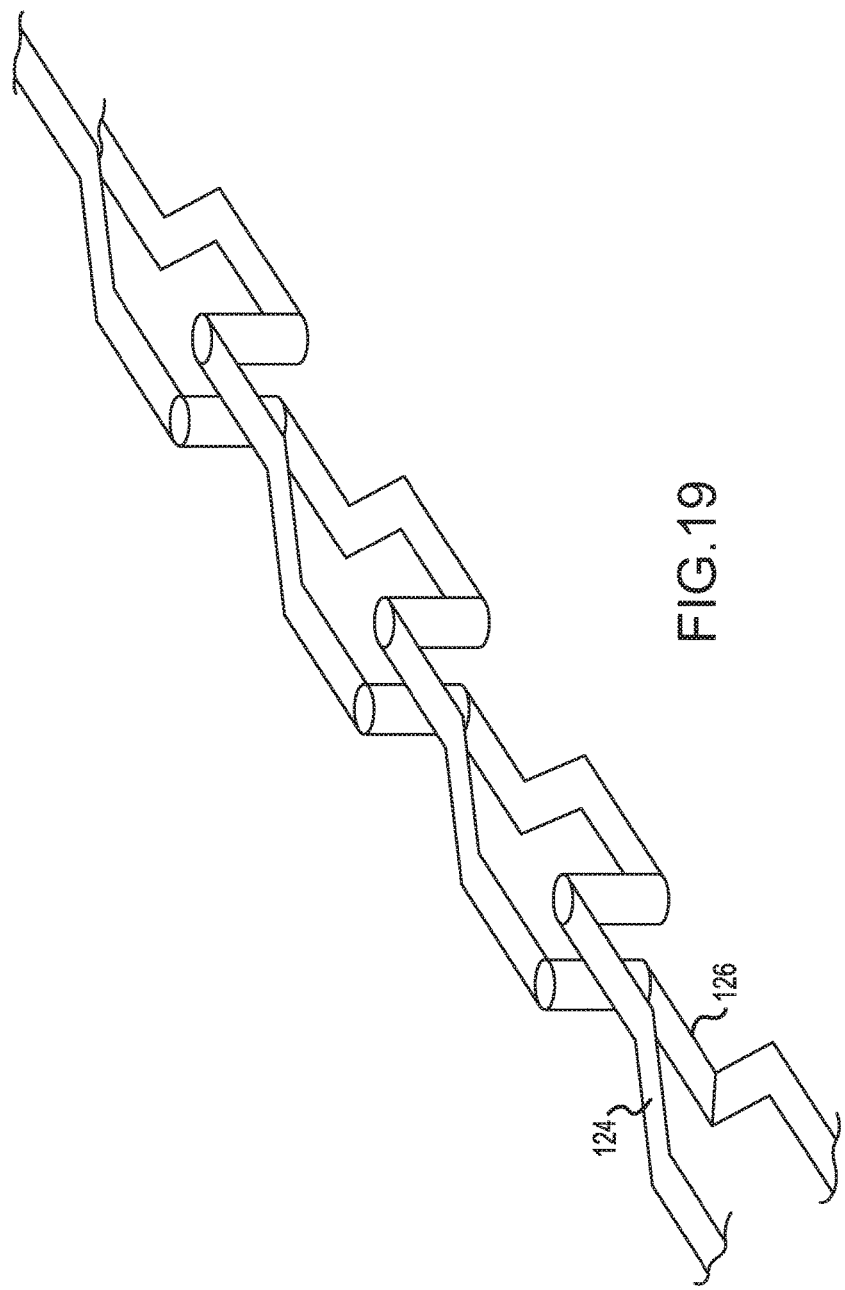
FIG. 19 is an isometric and diagrammatic view of an exemplary embodiment of a twisted differential line that may be implemented on the circuit board disposed within the junction box illustrated in FIG. 13 and formed of the signal and return traces thereof.

Alternatively, in another exemplary embodiment such as that illustrated in FIG. 19, and as is known in the art, the signal and return traces 124, 126 may be arranged as a twisted differential line that is formed on the circuit board 106 and between a pair of layers thereof, in particular. Generally speaking, in one such embodiment wherein the circuit board 106 has two layers, each layer of the circuit board 106 may comprise a plurality of portions of both the signal and return traces 124, 126 that may be electrically connected to form a single signal trace 124 and a single return trace 126 that are effectively arranged in a twisted pair pattern. For example, as illustrated in FIG. 19, the signal trace 124 may comprise a first portion disposed on a first layer of the circuit board 106, and a first portion of the return trace 126 disposed on a second layer of the circuit board 106, wherein the respective first portions of the signal and return traces are offset from each other (i.e., the first portions of the respective traces are not disposed in the same vertical or horizontal plane). As shown in FIG. 19, as the first portions of the signal and return traces extend along the length of the circuit board 106, they cross over/under each other and are electrically connected to respective electrically conductive pins extending between the two layers of the circuit board 106.

As illustrated in FIG. 19, the electrically conductive pins serve to electrically connect the first portion of the signal trace on the first layer of the circuit board 106 to a second portion of the signal trace disposed on the second layer of the circuit board 106, and the first portion of the return trace on the second layer of the circuit board 106 to a second layer of the return trace 126 disposed on the first layer of the circuit board 106. As with the first portions of the respective traces, as the second portions extend along the length of the circuit board 106, they cross over/under each other and are electrically connected to a second set of respective electrically conductive pins extending between the two layers of the circuit board 106. As with the pins to which the first portions of the signal and return traces are electrically connected, the second set of pins serve to electrically connect the second portions of the respective traces to third portions thereof disposed on the other layer of the circuit board 106. This arrangement may continue or be repeated any number of times until the signal and return traces 124, 126 are terminated as described elsewhere herein.

Another way to account for the creation of a loop on the circuit board 106 by the signal and return traces is to form a second magnetic loop on the circuit board 106 that is substantially equal in area and opposite in orientation to the first magnetic loop on the circuit board 106. As such, when the circuit board 106 is subjected or exposed to a magnetic field, the currents induced in the two magnetic loops will be equal but opposite, thereby resulting in the currents offsetting each other. Thus, interference to the signals generated by the sensor 28 and communicated over the traces of the circuit board 106 is prevented, or at least substantially minimized.

Figure 20:
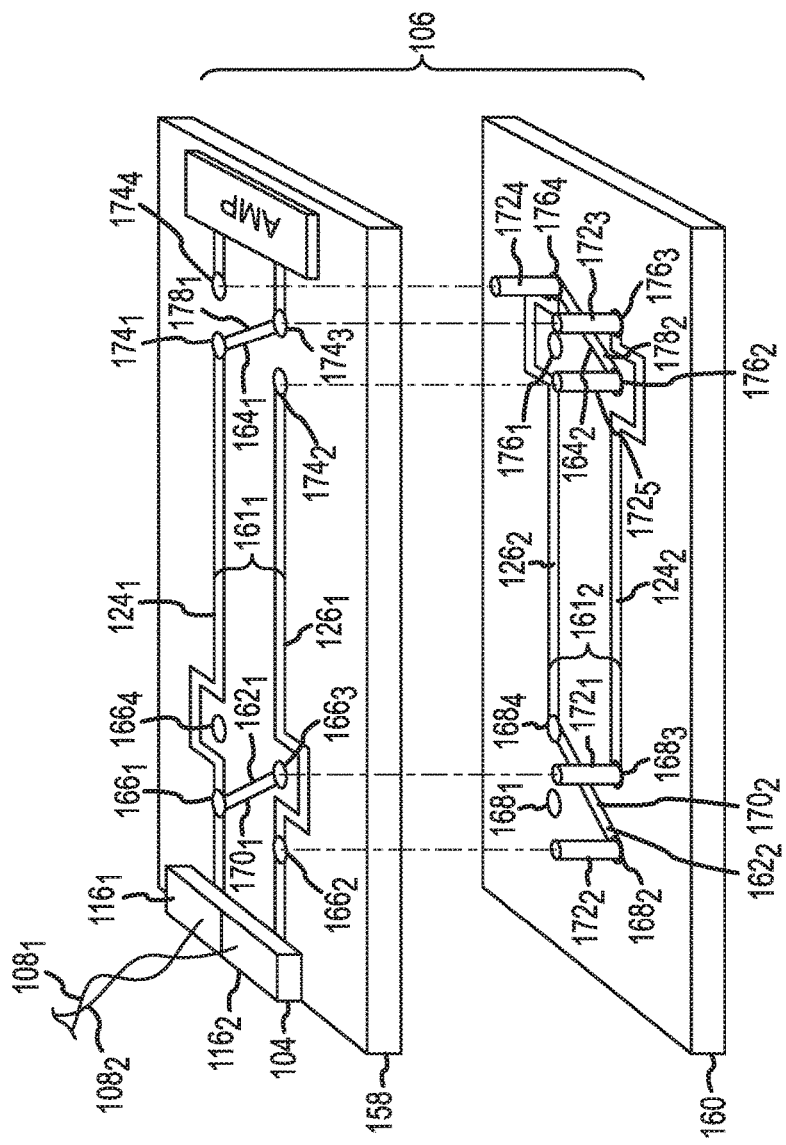
FIG. 20 is an isometric view of yet another exemplary embodiment of a circuit board configured to be disposed within the junction box illustrated in FIG. 13.

One such way in which this pair of magnetic loops may be formed is illustrated in FIG. 20. In such an embodiment, and as described above and illustrated in FIG. 13, a pair of wires $108_1$, $108_2$ electrically connect the pins $102_1$, $102_2$ of the connector 98, which, in turn, are respectively electrically connected to the leads $32_1$, $32_2$ of the sensor 28 through the combination of the connectors and cables described above, to corresponding sockets 116 of the header 104. In an exemplary embodiment, the socket $116_1$ of the header 104 to which the pin $102_1$ is connected serves to electrically connect the pin $102_1$ to a first signal trace $124_1$ on a first layer 158 of the circuit board 106. Similarly, the socket $116_2$ of the header 104 to which the pin $102_2$ is connected serves to electrically connect the pin $102_2$ to a first return trace $126_1$ on the first layer 158 of the circuit board 106. As will be described below, the first signal and return traces $124_1$, $126_1$ comprise, at least in part, a first magnetic loop $161_1$ on the circuit board 106.

With continued reference to FIG. 20, the circuit board 106 further comprises a second layer 160 having a second signal trace $124_2$ and a second return trace $126_2$ disposed thereon. The second signal trace $124_2$ is located directly below the first return trace $126_1$ of the first layer 158, while the second return trace $126_2$ is located directly below the first signal trace $124_1$ of the first layer 158. As will be described below, the second signal and return traces $124_2$, $126_2$ comprise, at least in part, a second magnetic loop $161_2$ on the circuit board 106.

The signal and return traces 124, 126 on each layer 158, 160 of the circuit board 106 are arranged such that they are opposite (and, in one embodiment, exactly opposite) to each other so that any magnetic pickup on the board 106 between the two traces $124_1$, $126_1$ on the first layer 158 is equal and opposite of the magnetic pickup between the two traces $124_2$, $126_2$ on the second layer 160. In other words, the two magnetic loops $161_1$, $161_2$ formed on the respective layers 158, 160 of the circuit board 106 are both substantially equal in area and opposite in orientation.

As illustrated in FIG. 20, to form the first and second magnetic loops $161_1$, $161_2$, a first pair of partial mechanical loops $162_1$, $162_2$ are formed between the first and second layers 158, 160 of the circuit board 106 at a first end thereof proximate the header 104, and a second pair of partial mechanical loops $164_1$, $164_2$ are also formed between the first and second layers 158, 160 of the circuit board 106 at a second end thereof opposite the first end and proximate either an amplifier (as shown in FIG. 20), an output port of the junction box 94, or the like.

More particularly, with respect to the first pair of partial mechanical loops $162_1$, $162_2$, the first layer 158 of the circuit board 106 comprises a first set of four through-holes $166_1$-$166_4$ arranged in a square, and the second layer 160 also comprises a first set of four through-holes $168_1$-$168_4$ that are also arranged in a square and that are aligned (and, in one embodiment, exactly aligned) with the first set of through-holes $166_1$-$166_4$ of the first layer 158. As illustrated in FIG. 20, an electrically conductive surface of the first through-hole $166_1$ of the first layer 158 is electrically connected to an electrically conductive element of the socket $116_1$ of the header 104 to which the pin $102_1$ of the connector 98 is connected. More particularly, a portion of the signal trace $124_1$ of the first layer 158 electrically connects the electrically conductive surface of the first through-hole $166_1$ to the electrically conductive element of the socket $116_1$.

As illustrated in FIG. 20, the third through-hole $166_3$ of the first layer 158 is disposed diagonal from the first through-hole $166_1$ and has an electrically conductive surface that is electrically connected to that of the first through-hole $166_1$ by way of a trace $170_1$ on the first layer 158 of the circuit board 106. In an exemplary embodiment, an electrically conductive pin $172_1$ is disposed within and extends between each of the third through-hole $166_3$ of the first layer 158 and the third through-hole $168_3$ of the second layer 160. The pin $172_1$ serves to electrically connect the electrically conductive surfaces of the through-holes $166_3$, $168_3$. As illustrated in FIG. 20, the electrically conductive surface of the third through-hole $168_3$ of the second layer 160 is electrically connected to the second signal trace $124_2$ that is disposed on the second layer 160. As a result of this arrangement, a first partial mechanical loop $162_1$ is formed between the first and second layers 158, 160 of the circuit board 106, and the first and second signal traces $124_1$, $124_2$ thereof.

A second partial mechanical loop $162_2$ may be formed in a similar way. More particularly, an electrically conductive surface of the second through-hole $166_2$ of the first layer 158 is electrically connected to an electrically conductive element of the socket $116_2$ of the header 104 to which the pin $102_2$ of the connector 98 is connected. More particularly, a portion of the return trace $126_1$ of the first layer 158 electrically connects the electrically conductive surface of the second through-hole $166_2$ to the electrically conductive element of the socket $116_2$.

In at least one exemplary embodiment, an electrically conductive pin $172_2$ is disposed within and extends between each of the second through-hole $166_2$ of the first layer 158 and the second through-hole $168_2$ of the second layer 160. The pin $172_2$ serves to electrically connect the electrically conductive surfaces of the through-holes $166_2$, $168_2$. The second through-hole $168_2$ of the second layer 160 is disposed diagonal from the fourth through-hole $168_4$ of the second layer 160, and has an electrically conductive surface that is electrically connected to that of the second through-hole $168_2$ of the second layer 160 by a trace $170_2$ on the second layer 160. The electrically conductive surface of the fourth through-hole $168_4$ of the second layer 160 is further electrically connected to the second return trace $126_2$ disposed on the second layer 160. As a result of this arrangement, a second partial mechanical loop $162_2$ is formed between the first and second layers 158, 160 of the circuit board 106, and the first and second return traces $126_1$, $126_2$ thereof.

With respect to the second pair of partial mechanical loops 164 disposed at the opposite end of the circuit board 106 from the first pair of partial mechanical loops 162, the first layer 158 of the circuit board 106 comprises a second set of four through-holes $174_1$-$174_4$ arranged in a square, and the second layer 160 also comprises a second set of four through-holes $176_1$-$176_4$ that are also arranged in a square and aligned (and, in one embodiment, exactly aligned) with the through-holes $174_1$-$174_4$ of the first layer 158.

As illustrated in FIG. 20, an electrically conductive surface of the third through-hole $176_3$ of the second layer 160 is electrically connected to the second signal trace $124_2$ of the second layer 160. In an exemplary embodiment, an electrically conductive pin $172_3$ is disposed within and extends between each of the third through-hole $176_3$ of the second layer 160 and the third through-hole $174_3$ of the first layer 158. The pin $172_3$ serves to electrically connect the electrically conductive surfaces of the through-holes $176_3$, $174_3$ The third through-hole $174_3$ of the first layer 158 is disposed diagonal from the first through-hole $174_1$ of the first layer 158 and the electrically conductive surface thereof is electrically connected to that of the first through-hole $174_1$ of the first layer 158 by a trace $178_1$ on the first layer 158. The electrically conductive surface of the first through-hole $174_1$ of the first layer 158 is further electrically connected to the first signal trace $124_1$ disposed on the first layer 158. It will be appreciated that the electrically conductive surface of third through-hole $174_3$ of the first layer 158 may be electrically connected to, for example, an amplifier or an output port of the junction box 94 (as shown), to allow for the further communication of the signal transmitted over the signal traces $124_1$, $124_2$ of the circuit board 106.

As a result of this arrangement, a first partial mechanical loop $164_1$ is formed between the first and second layers 158, 160 of the circuit board 106, and the first and second signal traces $124_1$, $124_2$ thereof.

A second partial loop $164_2$ may be formed in a similar way. As illustrated in FIG. 20, an electrically conductive surface of the fourth through-hole $176_4$ of the second layer 160 is electrically connected to the second return trace $126_2$ of the second layer 160. The second through-hole $176_2$ of the second layer 160 is disposed diagonally from the fourth through-hole $176_4$ of the second layer 160 and has an electrically conductive surface that is electrically connected to that of the fourth through-hole $176_4$ by way of a trace $178_2$ on the second layer 160 of the circuit board 106. In an exemplary embodiment, an electrically conductive pin $172_4$ is disposed within and extends between each of the fourth through-hole $176_4$ of the second layer 160 and the fourth through-hole $174_4$ of the first layer 158. The pin $172_4$ serves to electrically connect the electrically conductive surfaces of the through-holes $176_4$, $174_4$.

In an exemplary embodiment, an electrically conductive pin $172_5$ is also disposed within and extends between each of the second through-hole $176_2$ of the second layer 160 and the second through-hole $174_2$ of the first layer 158. The pin $172_5$ serves to electrically connect the electrically conductive surfaces of the through-holes $176_2$, $174_2$. As illustrated in FIG. 20, the electrically conductive surface of the second through-hole $174_2$ of the first layer 158 is electrically connected to the first return trace $126_1$ that is disposed on the first layer 158. It will be appreciated that the electrically conductive surface of fourth through-hole $174_4$ of the first layer 158 may be electrically connected to, for example, an amplifier (as shown) or an output port of the junction box 94, to allow for the extension of the return pathway from the circuit board 106.

As a result of this arrangement, a second partial mechanical loop $164_2$ is formed between the first and second layers 158, 160 of the circuit board 106, and the first and second return traces $126_1$, $126_2$ thereof, in particular.

The combination of the first and second partial mechanical loops 162, 164 result in the formation of the first complete magnetic loop $161_1$ on the first layer 158 of the circuit board 106 between the signal and return traces $124_1$, $126_1$, and the formation of the second complete magnetic loop $161_2$ on the second layer 160 of the circuit board 106 between the signal and return traces $124_2$, $126_2$. As described above, the first and second complete magnetic loops $161_1$, $161_2$ are both substantially equal in area and opposite in orientation so as to cancel out any current induced therein as a result of magnetic pickup.

It will be appreciated that the description of forming the partial mechanical loops 162, 164 or the resulting complete magnetic loops $161_1$, $161_2$ on the circuit board 106 set forth above may find application in connection with any of the embodiments described above relating to the creation of loops at the connection between the cable 34 and the junction box 94 (e.g., complementary partial loops created at the cable connector and the junction box connector, complementary partial loops created at the cable connector and on the circuit board 106, etc.), or elsewhere within the junction box 94, such as, for example, at the header 104 (e.g., complementary partial loops created on the top side of the header 104 and on the circuit board 106, for example).

As briefly described above, the junction box 94 may further comprise an output port in the form of an electromechanical connector (not shown). The connector is configured to provide an interface between the junction box 94 and one or more other components of the system 10. In an exemplary embodiment, the connector takes the same form as that of the connector 98. As such, the connector is electrically connected to one or more sets of signal and return traces on the circuit board 106, or the output of an amplifier disposed within the junction box 94. As with the connector 98, the output port connector may also comprise a plurality of partial magnetic loops that are configured to combine with partial magnetic loops of a cable connector when the output port connector and the complementary cable connector are mated. Accordingly, the description set forth above relating to the connector 98 applies here with equal force and will not be repeated. Rather, the description set forth above is incorporated here by reference.

In an alternate embodiment, rather than the output port connector of the junction box 94 comprising the partial magnetic loops that are complementary to those of a complementary cable connector configured to be mated therewith, the partial magnetic loops may be disposed on the circuit board 106 itself in the same manner as the partial magnetic loops $111_1'$, $111_2'$ illustrated in FIG. 14. Accordingly, the description set forth above relating to the embodiment wherein the partial magnetic loops 111' are disposed on the circuit board 106 applies here with equal force and will not be repeated. Rather, the description set forth above is incorporated here by reference.

As described elsewhere above, it will be appreciated that while the description of the output port of the junction box 94 has been primarily with respect to an embodiment wherein the connector is configured to accommodate a single-sensor catheter 12, the present disclosure is not meant to be so limited. Rather, in other exemplary embodiments, the junction box 94 may comprise one or more output port connectors, each configured to accommodate one or more single- or multiple-sensor catheters, and such embodiments remain within the spirit and scope of the present disclosure.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electromechanical connector for a medical device, for use in a magnetic field environment, comprising:
   a first end including a first plurality of electrical contacts;
   a second end including a second plurality of electrical contacts electrically coupled to the first plurality of electrical contacts;
   a first electrical jumper electrically coupling a first and a third electrical contact disposed at the first end to form a first partial loop;
   a second electrical jumper electrically coupling a second and a fourth electrical contact at the first end to form a second partial loop;
   a printed circuit board electrically coupled to each of the first, second, third, and fourth electrical contacts;
   wherein the first electrical jumper is a first electrical trace on the circuit board, and the second electrical jumper is a second electrical trace on the circuit board; and
   wherein the first and second partial loops are configured to reduce the pick-up of noise and interference by the electromechanical connector associated with the magnetic field environment.

2. The electromechanical connector of claim 1, wherein the first end is configured and arranged to mechanically and electrically coupled to an electrical cable;
   the electrical cable includes
   first and second electrical conductors extending across the electrical cable in a twisted pair arrangement,
   a first end of the electrical cable, configured to be mated with the first end of the electromechanical connector; and
   the first electrical conductor is electrically connected to a fifth electrical contact of the first plurality of electrical contacts and said second electrical conductor is electrically connected to a sixth electrical contact of the first plurality of electrical contacts;
   a third electrical jumper electrically connecting the fifth electrical contact with a seventh electrical contact of the first plurality of electrical contacts to form a third partial loop; and
   a fourth electrical jumper electrically connecting the sixth electrical contact with an eighth electrical contact of the first plurality of electrical contacts to form a fourth partial loop.

3. The electromechanical connector of claim 2, wherein the first and second partial loops of the connector are configured to combine with the respective third and fourth partial loops of said electrical cable when the connector is coupled with the cable to form first and second magnetic noise cancellation loops that are substantially equal in area and opposite in orientation.

4. The electromechanical connector of claim 3, wherein the first and second magnetic noise cancellation loops are configured and arranged to reduce the pick-up of noise and interference by the electromechanical connector.

5. The electromechanical connector of claim 1, wherein the first and second partial loops of are configured to combine with partial loops of a mating connector to form first and second magnetic noise cancellation loops that are substantially equal in area and opposite in orientation.

6. The electromechanical connector of claim 5, wherein the first and second magnetic noise cancellation loops are configured and arranged to reduce the pick-up of noise and interference by the electromechanical connector.

7. The electromechanical connector of claim 1, wherein the printed circuit board is a multi-layer printed circuit board,
   the first electrical trace, disposed on a first layer of the printed circuit board, coupling the first and thirds electrical contact and thereby forming the first partial loop, and
   the second electrical trace, disposed on a second layer of the printed circuit board, coupling the second and fourth electrical contacts and thereby forming the second partial loop.

8. The electromechanical connector of claim 1, wherein the printed circuit board includes
   a plurality of through-holes with an electrically conductive surfaces, the plurality of through-holes configured to receive the first plurality of electrical contacts, and electrically couple the first plurality of electrical contacts to the second plurality of electrical contacts via a plurality of traces on the printed circuit board.

9. The electromechanical connector of claim 1, further including lead wires that electrically couple the first plurality of electrical contacts to the second plurality of electrical contacts, the plurality of lead wires configured in a twisted pair arrangement.

10. The electromechanical connector of claim 1, wherein the first, second, third and fourth electrical contacts are arranged such that each electrical contact comprises a vertex of a square, and further wherein said first and third electrical contacts are diagonal from each other, and said second and fourth electrical contacts are diagonal from each other.

11. The electromechanical connector of claim 1, wherein the second partial magnetic loop is substantially parallel to said first partial magnetic loop.

12. The electromechanical connector of claim 1, wherein the first and second plurality of electrical contacts are selected from the group consisting of pins and sockets.

13. An electrical cable for a medical device, for use in a magnetic field environment, comprising:
    a first end including a first plurality of electrical contacts;
    a second end including a second plurality of electrical contacts;
    a multi-layer flexible printed circuit board extending from the first end to the second end; and
    a plurality of electrical traces and vias disposed on and between the multiple layers of the flexible printed circuit board, the plurality of electrical traces and vias configured and arranged
    in a twisted pair pattern that extends across the multiple layers of the flexible printed circuit board between the first and second ends,
    electrically coupling the first plurality of electrical contacts to the second plurality of electrical contacts; and
    wherein the twisted pair pattern of the plurality of electrical traces are configured to reduce the pick-up of noise and interference by the electrical cable associated with the magnetic field environment.

14. The electrical cable of claim 13, further including
    a first electrical trace, disposed on a first layer of the printed circuit board, electrically coupling a first and a third electrical contact disposed at the first end to form a first partial loop, a second electrical trace, disposed on a second layer of the printed circuit board, electrically coupling a second and a fourth electrical contact at the first end to form a second partial loop, and wherein the first and second electrical traces on the flexible printed circuit board electrically couple the first plurality of electrical contacts to the twisted pair pattern of electrical traces and vias extending from the first end to the second end of the printed circuit board.

15. The electrical cable of claim 14, wherein the first and second partial loops are configured to combine with partial loops of a mating connector to form first and second magnetic noise cancellation loops that are substantially equal in area and opposite in orientation.

16. The electrical cable of claim 15, wherein the first and second magnetic noise cancellation loops are configured and arranged to reduce the pick-up of noise and interference by the cable.

17. The electrical cable of claim 13, wherein the flexible printed circuit board includes a plurality of through-holes with electrically conductive surfaces near the first end of the flexible printed circuit board, the plurality of through-holes configured to receive the first plurality of electrical contacts, and electrically couple the first plurality of electrical contacts to the plurality of traces and vias on the flexible printed circuit board.

18. The electrical cable of claim 14, wherein the first, second, third and fourth electrical contacts are arranged such that each electrical contact comprises a vertex of a square, and further wherein said first and third electrical contacts are diagonal from each other, and said second and fourth electrical contacts are diagonal from each other.

19. The electrical cable of claim 14, wherein the second partial magnetic loop between said second and fourth electrical contacts is substantially parallel to said first partial magnetic loop between said first and third electrical contacts.

20. The electrical cable of claim 13, wherein the first and second plurality of electrical contacts are selected from the group consisting of pins and sockets.

* * * * *